United States Patent
Collias et al.

(10) Patent No.: US 12,036,098 B2
(45) Date of Patent: Jul. 16, 2024

(54) ABSORBENT HYGIENE PRODUCT COMPRISING SUPERABSORBENT POLYMER PARTLY DERIVED FROM A RECYCLED RESOURCE AND METHODS OF PRODUCING SAID PRODUCT

(71) Applicant: The Procter & Gamble Company, Cincinnati, OH (US)

(72) Inventors: Dimitris Ioannis Collias, Mason, OH (US); Martin Ian James, Hamilton, OH (US); Arsen Arsenov Simonyan, Schwalbach (DE)

(73) Assignee: The Procter & Gamble Company, Cincinnati, OH (US)

( * ) Notice: Subject to any disclaimer, the term of this patent is extended or adjusted under 35 U.S.C. 154(b) by 214 days.

(21) Appl. No.: 17/498,780

(22) Filed: Oct. 12, 2021

(65) Prior Publication Data
US 2022/0117800 A1    Apr. 21, 2022

Related U.S. Application Data

(60) Provisional application No. 63/092,617, filed on Oct. 16, 2020.

(51) Int. Cl.
*A61F 13/15* (2006.01)
*A61F 13/53* (2006.01)
(Continued)

(52) U.S. Cl.
CPC ........ *A61F 13/15577* (2013.01); *A61F 13/53* (2013.01); *A61F 13/551* (2013.01);
(Continued)

(58) Field of Classification Search
CPC ............... A61F 13/15577; A61F 13/53; A61F 2013/530744; A61F 2013/8497
See application file for complete search history.

(56) References Cited

U.S. PATENT DOCUMENTS

| 5,731,483 A | 3/1998 | Stabel et al. |
| 6,143,820 A | 11/2000 | Klier |

(Continued)

FOREIGN PATENT DOCUMENTS

| DE | 4204094 A1 | 8/1993 |
| EP | 1990106 A1 | 11/2008 |

(Continued)

OTHER PUBLICATIONS

Anita Gerina-Ancane et al. "Research and analysis of absorbent hygiene product (AHP) recycling", Engineering for Rural Development, Jelgava, 25-27, May 2016, 7 Pages.

(Continued)

*Primary Examiner* — Robert F Long
*Assistant Examiner* — Xavier A Madison
(74) *Attorney, Agent, or Firm* — Kathleen Y. Carter; James E. Oehlenschlager

(57) ABSTRACT

An AHP is disclosed having a topsheet, a backsheet joined with the topsheet, an absorbent core, disposed between the topsheet and the backsheet, and a poly(acrylic acid)-based superabsorbent polymer (SAP), partly derived from recycled resources. The SAP exhibits defined Saline Flow Conductivity and Absorption Against Pressure values. Methods for making the aforementioned AHP are also disclosed.

27 Claims, 7 Drawing Sheets

(51) Int. Cl.
*A61F 13/551* (2006.01)
*A61F 13/84* (2006.01)

(52) U.S. Cl.
CPC .. *A61F 13/84* (2013.01); *A61F 2013/530744* (2013.01); *A61F 2013/8497* (2013.01)

(56) References Cited

U.S. PATENT DOCUMENTS

| | | | |
|---|---|---|---|
| 6,180,845 | B1 | 1/2001 | Catallo et al. |
| 8,383,746 | B2 | 2/2013 | Torii |
| 9,095,853 | B2 | 8/2015 | Somma |
| 9,156,034 | B2 | 10/2015 | Somma |
| 9,822,203 | B2* | 11/2017 | Haag .................... C08F 2/10 |
| 2004/0034262 | A1 | 2/2004 | Van De Beld et al. |
| 2004/0232046 | A1 | 11/2004 | Tanaka et al. |
| 2006/0280669 | A1 | 12/2006 | Jones |
| 2009/0267349 | A1 | 10/2009 | Spitzauer et al. |
| 2009/0314700 | A1 | 12/2009 | Mabuchi |
| 2010/0180805 | A1 | 7/2010 | Cheiky |
| 2010/0221158 | A1 | 9/2010 | Kitamura et al. |
| 2010/0287825 | A1 | 11/2010 | Humphreys |
| 2011/0094674 | A1* | 4/2011 | Oetjen .................. B32B 5/08 156/277 |
| 2012/0302445 | A1 | 11/2012 | Rudolph et al. |
| 2013/0296619 | A1 | 11/2013 | Iaccino et al. |
| 2016/0237617 | A1* | 8/2016 | Yamaguchi ............ D21C 3/04 |
| 2016/0362609 | A1 | 12/2016 | Ward et al. |
| 2017/0198105 | A1* | 7/2017 | Lee ......................... C08J 3/245 |
| 2017/0226436 | A1 | 8/2017 | Gillespie et al. |
| 2017/0362512 | A1 | 12/2017 | Hornung et al. |
| 2019/0299181 | A1 | 10/2019 | Flynn et al. |
| 2020/0071619 | A1 | 3/2020 | Humphreys et al. |
| 2020/0149220 | A1 | 5/2020 | Konishi et al. |
| 2020/0238574 | A1* | 7/2020 | Konishi ................ D21H 11/14 |
| 2020/0369966 | A1 | 11/2020 | Bitting et al. |
| 2021/0130262 | A1 | 5/2021 | Wu et al. |
| 2021/0130699 | A1 | 5/2021 | Bitting et al. |
| 2022/0097279 | A1 | 3/2022 | Van Zijl et al. |
| 2022/0267561 | A1 | 8/2022 | Collias et al. |
| 2023/0332052 | A1 | 10/2023 | Collias et al. |
| 2023/0332053 | A1 | 10/2023 | Collias et al. |

FOREIGN PATENT DOCUMENTS

| | | | |
|---|---|---|---|
| EP | 3783054 | A1 | 2/2021 |
| EP | 3783056 | A1 | 2/2021 |
| JP | 2007007622 | A | 1/2007 |
| JP | 2013199626 | A | 10/2013 |
| KR | 102341361 | B1 | 12/2021 |
| WO | 2016151120 | A1 | 9/2016 |
| WO | 2021042113 | A1 | 3/2021 |
| WO | 2022011241 | A1 | 1/2022 |
| WO | 2022093523 | A1 | 5/2022 |

OTHER PUBLICATIONS

Yuriy Budyk et al. "Hydrothermal carbonization of disposable diapers", Journal of Environmental Chemical Engineering, vol. 7, Aug. 2, 2019, 7 pages.

All Office Actions; U.S. Appl. No. 17/678,707, filed Feb. 23, 2022.
Nakano Akihiko et al.,"Degradation of Aqueous Poly(acrylic Acid) and Its Sodium Salt Solutions by High-Speed Stirring", Journal of Applied Polymer Science, vol. 22, XP055927139, Retrieved from the internet: URL:https://onlinelibrary.wiley.com/doi/abs/10.1002/app.1978.070220813, Dated Apr. 1, 1978, pp. 2207-2215.
Search Report and Written Opinion for PCT/US2021/054361 dated Feb. 4, 2022,13 pages.
Ching Teck Wei et al: "Microwave-Assisted HydrothermalDecomposition of Super Absorbent Polymers", ACS Sustainable Chemistry & Engineering, vol. 8, No. 38, Aug. 31, 2020 (Aug. 31, 2020), pp. 14504-14510, XP055886586.
Odegard: "LCA of waste treatment of diaper material", XP055886650, May 30, 2018 (May 30, 2018), p. 37.Retrieved from the Internet: URL :https ://cedelft. eu/wp-content/uploads/sites/2/2021 /04/ CE_Delft_ 2M03_LCA_of_waste_treatment_of_diaper_material_Def. pdf[retrieved on Feb. 2, 2022].
Xinming Li et al: "Ultraviolet-induced decomposition of acrylicacid-based superabsorbent hydrogels crosslinked with N, N-methylenebisacrylamide", Journal of Applied Polymer Science, vol. 108, No. 6, (Jun. 15, 2008), pp. 3435-3441, XP055741088, US, ISSN: 0021-8995, DOI: 10.1002/app.27865.
All Office Actions; U.S. Appl. No. 17/498,781, filed Oct. 12, 2021.
All Office Actions; U.S. Appl. No. 17/498,783, filed Oct. 12, 2021.
Basedow, A. M., and Ebert, K. H, "Ultrasonic Degradation of Polymers in Solution", Advances in Polymer Science, 22, 1977, pp. 83-148.
Ebrahimi, R., et al., "The Study of Ultrasonic Degradation ofSuperabsorbent Hydrogels", Organic Chemistry International,20, 2012, Article ID 343768, doi:10.1155/2012/34376, pp. 1-5.
Jin et al. , Conversion of polyethylene waste into clean fuels and waxes via hydrothermal processing (HTP), https://doi.org/10.1016/j.fuel.2020.117726, Fuel 273 , (2020), 117726, pp. 1-11.
Jin et al. , Low-pressure hydrothermal processing of mixed polyolefin wastes into clean fuels, https://doi.org/10.1016/j.fuel.2021.120505, fuel 294, 2021,120505, pp. 1-9.
Prajapat, A. L., and Gogate, P. R.,"Ultrasonics Sonochemistry", vol. 32,2016, pp. 290-299.
Shukla, N. B., and Madras, G., "Photo, Thermal, and Ultrasonic Degradation of EGDMA-Crosslinked Poly(acrylic acid-co-sodium acrylate-co-acrylamide) Superabsorbents", Journal of Applied Polymer Science, vol. 125, 2012, pp. 630-639.
Shukla, N. B., et al., "Ultrasonic Degradation of Poly(acrylic acid)", Journal of Applied Polymer Science, vol. 112, Jan. 23, 2009, pp. 991-997.
U.S. Appl. No. 17/498,781, filed Oct. 12, 2021, to Dimitris Ioannis Collias et. al.
U.S. Appl. No. 17/498,783, filed Oct. 12, 2021, to Dimitris Ioannis Collias et. al.
Adebayo-Ige et al. "Mixed Plastics Waste to Ethylene and Propylene Feedstocks", Senior Design Reports (CBE), University of Pennsylvania, Scholarly Commons, Department of Chemical & Biomolecular Engineering, Apr. 21, 2020, 269 pages.
Xu et al., "Hydrothermal Liquefaction of Biomass in Hot-Compressed Water, Alcohols, and Alcohol-Water Co-solvents for Biocrude Production", Application of Hydrothermal Reactions to Biomass Conversion, Green Chemistry and Sustainable Technology, Chapter 8, Jan. 1, 2014, pp. 171-187.
Soni, et al., "Thermochemical Recycling of Waste Plastics by Pyrolysis: A Review", In Journal of Energy & Fuels, vol. 35, Issue 16, Aug. 19, 2021, pp. 12763-12808.

* cited by examiner

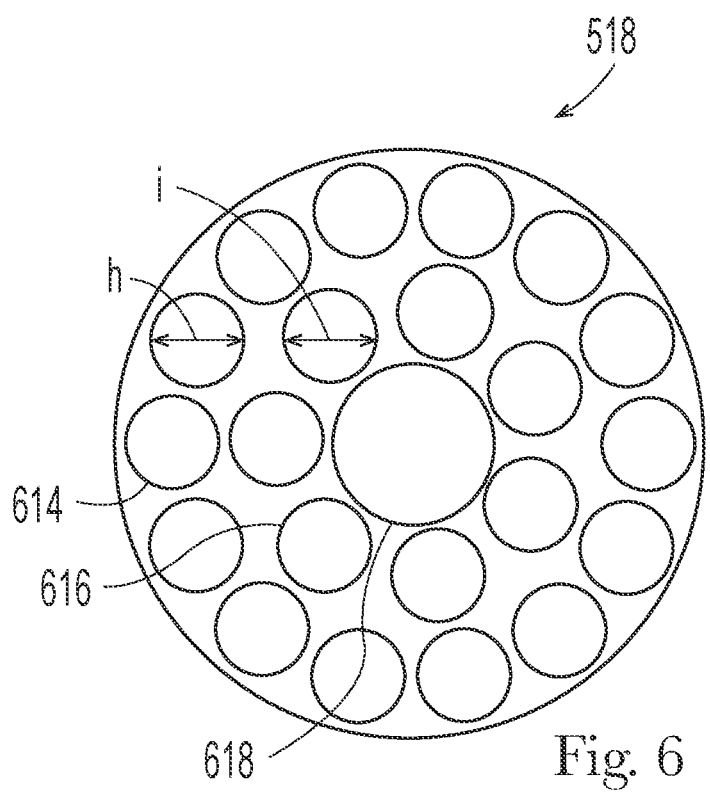
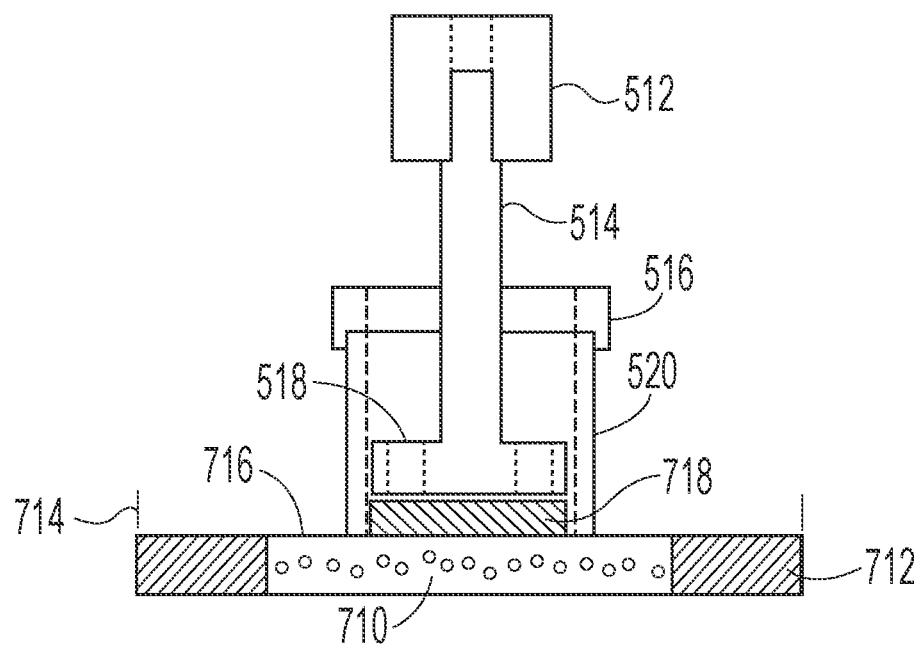
Fig. 6
Fig. 7

ABSORBENT HYGIENE PRODUCT COMPRISING SUPERABSORBENT POLYMER PARTLY DERIVED FROM A RECYCLED RESOURCE AND METHODS OF PRODUCING SAID PRODUCT

FIELD OF INVENTION

The present invention relates to an absorbent hygiene product (AHP) comprising a superabsorbent polymer (cycloSAP) derived from the polymerization of acrylic acid in the presence of poly(acrylic acid) (PAA). This PAA is produced from recycled superabsorbent polymer (rSAP) via a degradation process and is essentially a non-crosslinked linear or slightly branched molecule. CycloSAP has the same properties as virgin SAP (i.e., SAP derived from the polymerization of 100% acrylic acid; vSAP). Finally, the rSAP is separated from a recycled AHP (rAHP) and then degraded to PAA.

BACKGROUND OF THE INVENTION

Many consumers demand and expect companies to produce products that include recycled materials, which are materials derived from recycled resources, and subjected to processing (optionally) and purification in order to be re-useable. In some instances, consumers are hesitant to purchase products made only from limited non-renewable resources, such as petroleum, natural gas, and coal. Other consumers may have adverse perceptions about products that do not include recycled materials as not being environmentally friendly.

Recycling of AHPs (i.e., baby diapers, feminine protection pads, and adult incontinence pads) is good for the environment and needed to achieve the sustainability goals of many consumer companies. These goals are about using 100% recycled materials and having zero consumer and manufacturing waste go to landfill. In addition to these goals, successful recycling benefits the environment, stimulates the economy, improves people's health and water quality, and generates energy needed by consumers in developing regions of the world.

The major component in AHPs is typically the superabsorbent polymer (SAP), whereas other components are adhesives, cellulose fibers, polyethylene, polypropylene, and polyester. SAP is a water-absorbing, water-swellable, and water-insoluble powdered solid which is typically a crosslinked and partially neutralized homopolymer of glacial acrylic acid. SAP has an exceptionally high ability to absorb aqueous liquids, such as contaminated water or urine. About 97% of SAP produced today is used in AHP applications, whereas the remainder 3% is used in other applications, such as agricultural or horticultural water-retaining agents, and industrial waterproofing agents.

Recycling of AHPs involves collecting recycled AHPs, cleaning them from the soils accumulated during their use, and separating the various components into recycled material streams. More specifically, the recycled SAP material stream can be used in applications less demanding than AHPs (since the recycled SAP has inferior properties compared to virgin SAP; for example, agricultural or horticultural water-retaining agents, and industrial waterproofing agents) and/or can be converted to PAA. Then, this PAA can be used as a feed material to various applications. For example, the PAA can be: 1) used as-is in applications, such as water treatment or corrosion inhibition; 2) esterified and then used in adhesives, coatings, etc.; and 3) blended with acrylic acid as it is polymerized and crosslinked into SAP. The first two sets of applications are part of the effort to recycle SAP into other products by replacing virgin acrylic-acid-based compounds with compounds derived from recycled SAP, whereas the last set of applications is part of the circular economy of SAP, i.e., recycling SAP back to SAP. In all cases, the objective is to achieve the same properties as virgin materials.

Non-limiting examples of processes that produce purified and separated material streams of used SAP from recycled AHPs are disclosed and claimed in U.S. Pat. Nos. 9,095,853 and 9,156,034, both assigned to Fater S.p.A, based in Pescara, Italy. Non-limiting examples of procedures used to produce SAPs from glacial acrylic acid and crosslinkers are disclosed in U.S. Pat. No. 8,383,746 assigned to Nippon Shokubai Co., Ltd, based in Osaka, Japan; and U.S. Pat. No. 9,822,203 assigned to BASF SE, based in Ludwigshafen, Germany.

Accordingly, there is a need to recycle AHPs and their major component, which is SAP. For the recycling of SAP, there is a need to degrade recycled SAP into poly(acrylic acid) (PAA), in short time scale; with low energy and power per unit mass of SAP; and at mild conditions, such as room temperature, thus avoiding decarboxylation of the PAA. The requirement for low energy per unit mass of SAP stems from the fact that the recycling of SAP and its degradation to PAA is beneficial only if the energy spent during the converting of SAP to PAA is less than that used to make fossil-derived acrylic acid (petro-AA) from propylene, which is about 50 MJ/kg AA. The PAA produced from recycled SAP can then be incorporated back into virgin SAP (thus increasing its recycled content and supporting the circular economy of SAP) and/or derivatized into materials for other applications, such as, adhesives, coatings, water treatment, fabric care, etc. Also, it would be desirable to provide an AHP which comprises an SAP, which is partly derived from recycled resource, where the superabsorbent polymer has the same properties as virgin SAP. Ideally, it would be desirable to provide an AHP with an SAP which is partly derived from recycled resource and a communication of a related environmental message.

SUMMARY OF THE INVENTION

In one embodiment of the present invention, a method for providing an absorbent hygiene product (AHP) to a consumer is presented. The method comprises: a) providing a superabsorbent polymer (SAP) made by the steps of: (i) separating a recycled SAP (rSAP) from a recycled AHP (rAHP); (ii) degrading said rSAP to a material comprising poly(acrylic acid) (PAA); and (iii) polymerizing an acrylic acid in the presence of said PAA to form said SAP exhibiting an Absorption Against Pressure (AAP) of at least about 15 g/g; b) combining said SAP with AHP components comprising a topsheet and a backsheet to define said AHP; c) disposing said AHP into a package; and d) communicating an environmental message to said consumer to convey that said AHP comprises material derived from a recycled resource.

In another embodiment of the present invention, a method for providing an AHP to a consumer is presented. The method comprises: a) a) providing a superabsorbent polymer (SAP) made by the steps of: (i) separating a recycled SAP (rSAP) from a recycled AHP (rAHP); (ii) degrading said rSAP to a material comprising poly(acrylic acid) (PAA) via processing in an extensional flow device; and (iii) polymerizing an acrylic acid in the presence of said PAA to form said SAP exhibiting an Absorption Against Pressure (AAP) of at least about 15 g/g and a saline flow conductivity (SFC) of at least about 30×10$^{-7}$ cm$^3$·s/g; b) combining said SAP with AHP components comprising a topsheet and a backsheet to define said AHP; c) disposing said AHP into a package; and d) communicating an environmental message to said consumer to convey that said AHP comprises material derived from a recycled resource.

BRIEF DESCRIPTION OF THE DRAWINGS

FIG. 6 is a top view of a piston head suitable for use in the piston/cylinder assembly shown in FIG. 5.

FIG. 7 is a cross-sectional side view of the piston/cylinder assembly of FIG. 5 placed on a fritted disc for the swelling phase.

DETAILED DESCRIPTION OF THE INVENTION

I. Definitions

Figure 1A:
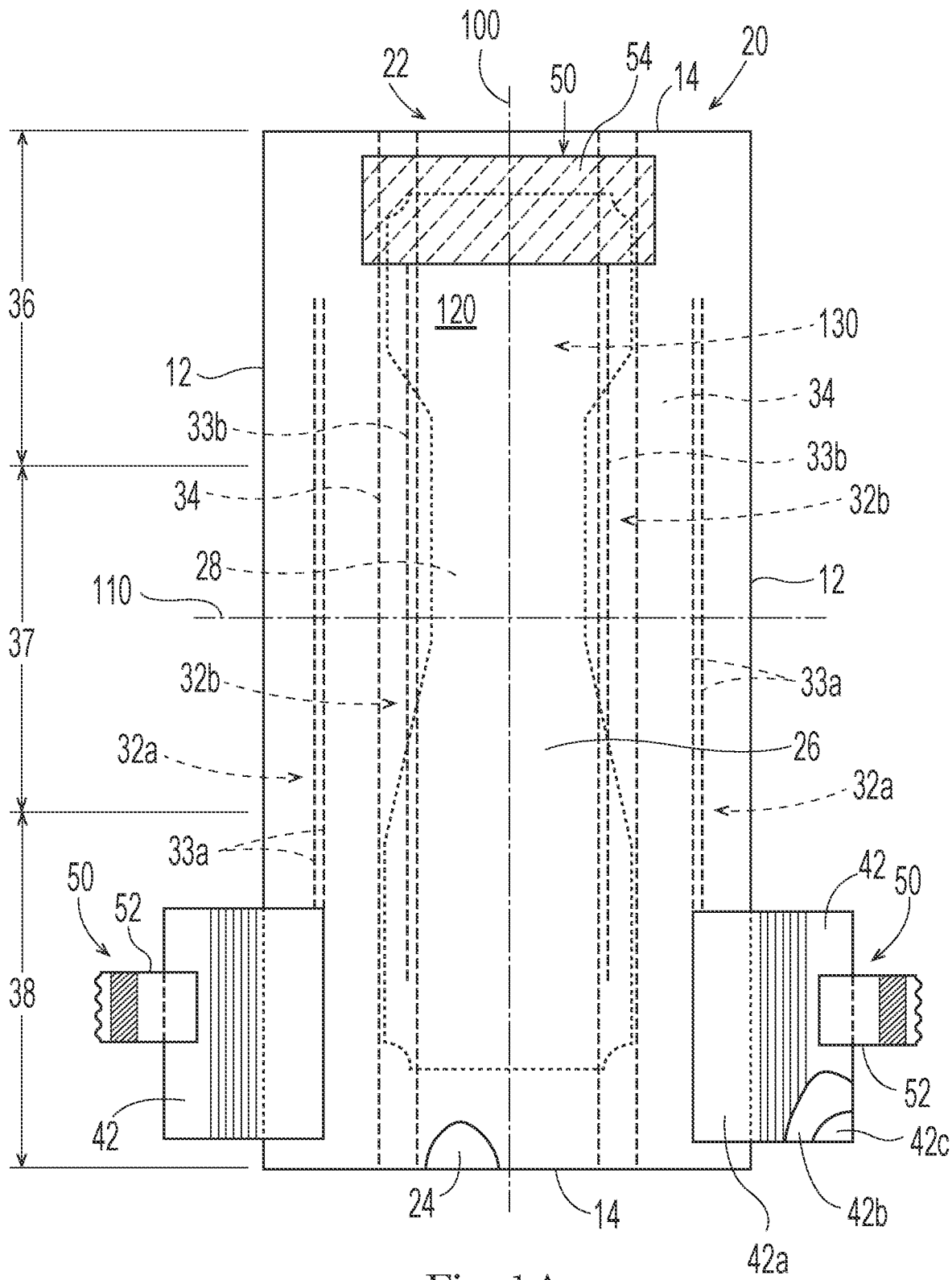
FIG. 1A is a plan view of an exemplary AHP in the form of a diaper in a flat, uncontracted state.

As used herein, the term "disposable" refers to items that are intended to be discarded after a limited number of uses, frequently a single use (i.e., the original AHP as a whole is not intended to be laundered or reused as an AHP, although certain materials or portions of the AHP may be recycled, reused, or composted). For example, certain disposable AHPs may be temporarily restored to substantially full functionality through the use of removable/replaceable components, but the AHP is nevertheless considered to be disposable because the entire AHP is intended to be discarded after a limited number of uses.

As used herein, the term "absorbent hygiene product (AHP)" refers to a product which absorbs and contains body exudates and, more specifically, refers to a product which is placed against or in proximity to the body of the wearer to absorb and contain the various exudates discharged from the body. Exemplary AHPs include diapers, training pants, pull-on pant-type diapers (i.e., a diaper having a pre-formed waist opening and leg openings, such as illustrated in U.S. Pat. No. 6,120,487), re-fastenable diapers or pant-type diapers, incontinence briefs and undergarments, diaper holders and liners, feminine hygiene garments, such as panty liners (e.g. such as disclosed in U.S. Pat. Nos. 4,425,130; 4,687,478; 5,267,992; and 5,733,274), absorbent inserts, and the like. AHPs may be disposable or may contain portions that can be reused or restored.

As used herein, the terms "proximal" and "distal" refer, respectively, to the location of an element relatively near to or far from the longitudinal or lateral centerline of a structure (e.g., the proximal edge of a longitudinally extending element is located nearer to the longitudinal centerline than the distal edge of the same element is located relative to the same longitudinal centerline).

As used herein, the terms "body-facing" and "garment-facing" refer, respectively, to the relative location of an element or a surface of an element or group of elements. "Body-facing" implies the element or surface is nearer to the wearer during wear than some other element or surface. "Garment-facing" implies the element or surface is more remote from the wearer during wear than some other element or surface (i.e., element or surface is proximate to the wearer's garments that may be worn over the AHP).

As used herein, the term "superabsorbent polymer (SAP)" refers to a polymer capable of absorbing at least ten times its dry weight of a 0.9% saline solution at 25° C. SAPs absorb fluid via an osmotic mechanism to form a gel, often referred to as, and used interchangeably with the term, "hydrogel".

As used herein, the term "longitudinal" refers to a direction running substantially perpendicular from a waist edge to an opposing waist edge of the product and generally parallel to the maximum linear dimension of the product. Directions within 45 degrees of the longitudinal direction are considered to be "longitudinal".

As used herein, the term "lateral" refers to a direction running from a longitudinal edge to an opposing longitudinal edge of the product and generally at a right angle to the longitudinal direction. Directions within 45 degrees of the lateral direction are considered to be "lateral."

As used herein, the term "disposed" refers to an element being located in a particular place or position.

As used herein, the term "joined" refers to configurations whereby an element is directly secured to another element by affixing the element directly to the other element and to configurations whereby an element is indirectly secured to another element by affixing the element to intermediate member(s) which in turn are affixed to the other element.

As used herein, the term "film" refers to a sheet-like material wherein the length and width of the material far exceed the thickness of the material. Typically, films have a thickness of about 0.5 mm or less.

As used herein, the term "impermeable" generally refers to products and/or elements that are not penetrative by fluid through the entire Z-directional thickness of the product under pressure of 0.14 lb/in.$^2$ or less. Preferably, the impermeable product or element is not penetrative by fluid under pressures of 0.5 lb/in.$^2$ or less. More preferably, the impermeable product or element is not penetrative by fluid under pressures of 1.0 lb/in.$^2$ or less. The test method for determining impermeability conforms to EDANA 120.1-18 or INDA IST 80.6.

As used herein, the terms "extensibility" and "extensible" mean that the width or length of the component in a relaxed state can be extended or increased by at least about 10% without breaking or rupturing when subjected to a tensile force.

As used herein, the terms "elastic," "elastomer," and "elastomeric" refer to a material which generally is able to extend to a strain of at least 50% without breaking or rupturing and is able to recover substantially to its original dimensions after the deforming force has been removed.

As used herein, the term "elastomeric material" is a material exhibiting elastic properties. Elastomeric materials may include elastomeric films, scrims, nonwovens, and other sheet-like structures.

As used herein, the terms "outboard" and "inboard" refer, respectively, to the location of an element disposed relatively far from or near to the longitudinal centerline of the diaper with respect to a second element. For example, if element A is outboard of element B, then element A is farther from the longitudinal centerline than is element B.

As used herein, the term "pant" refers to an AHP having a pre-formed waist and leg openings. A pant may be donned by inserting a wearer's legs into the leg openings and sliding the pant into position about the wearer's lower torso. Pants are also commonly referred to as "closed diapers", "pre-fastened diapers", "pull-on diapers", "training pants" and "diaper-pants."

As used herein, the term "petrochemical" refers to an organic compound derived from petroleum, natural gas, or coal.

As used herein, the term "petroleum" refers to crude oil and its components of paraffinic, cyclo paraffinic, and aromatic hydrocarbons. Crude oil may be obtained from tar sands, bitumen fields, and oil shale.

As used herein, the term "renewable resource" refers to a natural resource that can be replenished within a 100-year time frame. The resource may be replenished naturally, or via agricultural techniques. Renewable resources include plants, animals, fish, bacteria, fungi, and forestry products. They may be naturally occurring, hybrids, or genetically engineered organisms. Natural resources such as crude oil, coal, and peat which take longer than 100 years to form are not considered to be renewable resources As used herein, the term "agricultural product" refers to a renewable resource resulting from the cultivation of land (e.g. a crop) or the husbandry of animals (including fish).

As used herein, the term "monomeric compound" refers to an intermediate compound that may be polymerized to yield a polymer.

As used herein, the term "polymer" refers to a macromolecule comprising repeat units where the macromolecule has a molecular weight of at least 1000 g/mol. The polymer may be a homopolymer, copolymer, terpolymer, etc. The polymer may be produced via fee radical, condensation, anionic, cationic, Ziegler-Natta, metallocene, or ring-opening mechanisms. The polymer may be linear, branched and/or crosslinked.

As used herein, the term "synthetic polymer" refers to a polymer which is produced from at least one monomer by a chemical process. A synthetic polymer is not produced directly by a living organism. For the purposes of the present invention, the terms "synthetic polymer" and "polymer" are used interchangeably.

As used herein, the terms "polyethylene" and "polypropylene" refer to polymers prepared from ethylene and propylene, respectively. The polymer may be a homopolymer or may contain up to about 10 mol % of repeat units from a co-monomer.

As used herein, the term "communication" refers to a medium or means by which information, teachings, or messages are transmitted.

As used herein, the term "related environmental message" refers to a message that conveys the benefits or advantages of the AHP comprising a polymer derived from a recycled resource. Such benefits include being more environmentally friendly, having reduced petroleum dependence, being derived from recycled resources, and the like.

As used herein, the term "recycled AHP" refers to an AHP that was used for a previous purpose and then collected for the purpose of recycling.

As used herein, the term "recycled SAP (rSAP)" refers to an SAP that was used for a previous purpose, collected for the purpose of recycling (as part of the collected AHP that the SAP is part of), and then prepared for the degradation process.

As used herein, the term "degraded SAP" refers to a recycled SAP that has been degraded. For the purposes of the present invention, the degraded SAP is PAA and the two terms are used interchangeably. The degradation could involve de-crosslinking of the SAP, breaking of the cross-linked PAA chains into smaller fragments, or a combination of both.

As used herein, the term "cycloSAP" refers to an SAP derived from the polymerization of (virgin) acrylic acid in the presence of PAA using the same process as when making SAP from virgin acrylic acid only.

All percentages herein are by weight unless specified otherwise.

II. Degraded SAP (or PAA)

Degraded SAP (or PAA) can be produced from SAP via many methods. Non-limiting examples of SAP degradation methods are processing: in an extensional flow device (e.g. U.S. Patent Application No. 62/890,631); using hydrothermal microwave (e.g. U.S. Patent Application No. 62/890, 632); using UV irradiation in a flow system (e.g. U.S. patent application Ser. No. 16/548,873); using sonication/ultrasonics (e.g. U.S. Patent Application No. 62/890,880), using oxidative degradation; using hydrothermal treatment; using a combination of an extensional flow device, oxidative degradation, and enzymatic degradation (e.g. U.S. Patent Application No. 63/039,496); using an extensional flow device and oxidative degradation (e.g. U.S. Patent Application No. 63/039,498); and any combination thereof.

In one embodiment of the present invention, the PAA has a weight-average molecular weight less than about 5,000,000 g/mol. In another embodiment of the present invention, the PAA has a weight-average molecular weight less than about 2,000,000 g/mol. In yet another embodiment of the present invention, the PAA has a weight-average molecular weight less than about 1,000,000 g/mol. In even yet another embodiment of the present invention, the PAA has a weight-average molecular weight less than about 500,000 g/mol. In one embodiment of the present invention, the PAA has a weight-average molecular weight less than about 300,000 g/mol. In another embodiment of the present invention, the PAA has a weight-average molecular weight less than about 200,000 g/mol. In yet another embodiment of the present invention, the PAA has a weight-average molecular weight less than about 100,000 g/mol. In even yet another embodiment of the present invention, the PAA has a weight-average molecular weight less than about 30,000 g/mol.

In one embodiment of the present invention, the PAA has a weight-average molecular weight between about 1,000,000 g/mol and about 5,000,000 g/mol. In another embodiment of the present invention, the PAA has a weight-average molecular weight between about 500,000 g/mol and about 2,000,000 g/mol. In yet another embodiment of the present invention, the PAA has a weight-average molecular weight between about 100,000 g/mol and about 1,000,000 g/mol. In even yet another embodiment of the present invention, the PAA has a weight-average molecular weight between about 150,000 g/mol and about 500,000 g/mol. In one embodiment of the present invention, the PAA has a weight-average molecular weight between about 90,000 g/mol and about 300,000 g/mol. In another embodiment of the present invention, the PAA has a weight-average molecular weight between about 20,000 g/mol and about 200,000 g/mol. In yet another embodiment of the present invention, the PAA has a weight-average molecular weight between about 10,000 g/mol and about 100,000 g/mol.

In one embodiment of the present invention, the PAA has a polydispersity index (PDI) less than about 10. In another embodiment of the present invention, the PAA has a PDI less than about 6. In yet another embodiment of the present invention, the PAA has a PDI less than about 4. In even yet another embodiment of the present invention, the PAA has a PDI less than about 2. PDI is the ratio of the weight-average molecular weight to the number-average molecular weight, and these molecular weights are measured by Gel Permeation Chromatography (GPC), as it is well known to those skilled in the art.

In one embodiment of the present invention, a method for providing an absorbent hygiene product (AHP) to a consumer comprises: a) providing a superabsorbent polymer (rSAP) made by the steps of: (i) separating a recycled SAP (rSAP) from a recycled AHP (rAHP); and (ii) degrading said rSAP to a degraded material comprising poly(acrylic acid) (PAA). In another embodiment of the present invention, the degrading comprises UV irradiation in a flow system. In yet another embodiment of the present invention, the degrading comprises processing in an extensional flow device. In yet another embodiment of the present invention, the degrading comprises microwave-assisted hydrothermal processing. In even yet another embodiment of the present invention, the degrading comprises sonication. In one embodiment of the present invention, the degrading comprises oxidative degradation.

III. CycloSAP

A. SAPs useful in the present invention can be formed by any polymerization and crosslinking techniques capable of achieving the desired product properties. Typical methods for producing these polymers are described in Reissue U.S. Pat. No. 32,649; U.S. Pat. Nos. 4,666,983; 4,625,001; and 5,408,019; and German Patent Application No. 4,020,780. The processing (i.e., drying, milling, sieving, etc.) of the resulting SAP to yield a usable form is well known to those skilled in the art.

The polymer may be prepared in the neutralized, partially neutralized, or un-neutralized form. In one embodiment of the present invention, the acrylic acid is neutralized from about 50 mol % to about 95 mol %. In another embodiment of the present invention, the acrylic acid is neutralized from about 60 mol % to about 80 mol %. In yet another embodiment of the present invention, the acrylic acid is neutralized about 67 mol %.

The SAP may be prepared using a homogeneous solution polymerization process, or by multi-phase polymerization techniques, such as inverse emulsion or suspension polymerization procedures. The polymerization reaction will generally occur in the presence of a relatively small amount of di- or poly-functional monomers, such as N,N'-methylene bisacrylamide, trimethylolpropane triacrylate, ethylene glycol di(meth)acrylate, triallylamine, and methacrylate analogs of the aforementioned acrylates. The di- or poly-functional monomer compounds serve to lightly cross-link the polymer chains thereby rendering them water-insoluble, yet water-swellable. In one embodiment of the present invention, the SAP is formed using a homogeneous solution polymerization process. In another embodiment of the present invention, the SAP is formed using a multi-phase polymerization process. In yet another embodiment of the present invention, the multi-phase polymerization process is selected from the group consisting of inverse emulsion processes and suspension polymerization processes. In one embodiment of the present invention, the SAP is formed by polymerization in the presence of a di- or poly-functional monomer.

In one embodiment of the present invention, the SAP is produced from acrylic acid and PAA. In another embodiment of the present invention, the acrylic acid is produced from fossil-derived propylene. In yet another embodiment of the present invention, the acrylic acid is produced from renewable resources. In even yet another embodiment of the present invention, the acrylic acid is produced from lactic acid. In one embodiment of the present invention, the SAP is produced from acrylic acid and PAA; wherein said acrylic acid is produced from fossil-derived propylene; and wherein said PAA is degraded SAP. In another embodiment of the present invention, the SAP is produced from acrylic acid and PAA; wherein said acrylic acid is produced from renewable resources; and wherein said PAA is degraded SAP. In yet another embodiment of the present invention, the SAP is produced from acrylic acid and PAA; wherein said acrylic acid is produced from lactic acid; and wherein said PAA is degraded SAP. In even yet another embodiment of the present invention, the SAP is produced from acrylic acid and PAA; wherein said acrylic acid is produced from renewable propylene; and wherein said PAA is degraded SAP.

Non-limiting examples of renewable resources used to make acrylic acid or propylene are sugar (from corn, sugarcane, etc.), lactic acid or its derivatives made from sugar, glycerin, 3-hydroxypropionic acid or its derivatives made from sugar, starch, starch-acrylic acid graft copolymers, itaconic acid from sugar, ethylene from sugar (via fermentation and dehydration), etc. Examples of preparation of some of these materials are disclosed in U.S. Pat. Nos. 3,661,875; 4,076,663; 4,093,776; 4,666,983; 4,734,478; 8,884,050; 9,611,208; and 10,723,689.

The SAP particles can be surface-crosslinked after polymerization by reaction with a suitable reactive crosslinking agent. Surface-crosslinking of the initially formed SAP particles, derived from recycled resources, provides SAPs having relatively high absorbent capacity and relatively high permeability to fluid in the swollen state, as described below. A number of processes for introducing surface crosslinking are disclosed in the art. Suitable methods for surface cross-linking are disclosed in U.S. Pat. Nos. 4,541,871; 4,824,901; 4,789,861; 4,587,308; 4,734,478; and 5,164,459; PCT Application Nos. WO92/16565; WO90/08789; and WO93/05080; German Patent Application No. 4,020,780; and European Patent Application No. 509,708. Suitable cross-linking agents include di- or poly-functional crosslinking reagents, such as di/poly-haloalkanes, di/poly-epoxides, di/poly-acid chlorides, di/poly-tosyl alkanes, di/poly-aldehydes, di/poly-alcohols, and the like. In one embodiment of the present invention, the method further comprises surface crosslinking of said SAP. In another embodiment of the present invention, the method further comprises surface crosslinking of said SAP, the acrylic acid is neutralized from about 50 mol % to about 95 mol %, and the SAP is formed using a homogeneous solution polymerization in the presence of a di- or poly-functional monomer.

An important characteristic of the SAPs of the present invention is the permeability or flow conductivity of a zone or layer of the SAP particles when swollen with body fluids. This permeability or flow conductivity is defined herein in terms of the Saline Flow Conductivity (SFC) value of the SAP. SFC measures the ability of the swollen hydrogel zone or layer to transport or distribute body fluids under usage pressures. It is believed that when an SAP is present at high concentrations in an absorbent member and then swells to form a hydrogel under usage pressures, the boundaries of the hydrogel come into contact, and interstitial voids in this high-concentration region become generally bounded by hydrogel. When this occurs, it is believed that the permeability or flow conductivity properties of this region are generally reflective of the permeability or flow conductivity properties of a hydrogel zone or layer formed from the SAP alone. It is further believed that increasing the permeability of these swollen high-concentration regions to levels that approach or even exceed conventional acquisition/distribution materials, such as wood-pulp fluff, can provide superior fluid handling properties for the absorbent member and absorbent core, thus decreasing incidents of leakage, especially at high fluid loadings. Higher SFC values also are reflective of the ability of the formed hydrogel to acquire body fluids under normal usage conditions.

In one embodiment of the present invention, the SFC of the SAP is from about $30 \times 10^{-7}$ to about $1,000 \times 10^{-7}$ cm$^3 \cdot$s/g. In another embodiment of the present invention, the SFC of the SAP is from about $50 \times 10^{-7}$ to about $500 \times 10^{-7}$ cm$^3 \cdot$s/g. In yet another embodiment of the present invention, the SFC of the SAP is from about $100 \times 10^{-7}$ to about $350 \times 10^{-7}$ cm$^3 \cdot$s/g. In one embodiment of the present invention, the SFC of the SAP is at least about $30 \times 10^{-7}$ cm$^3 \cdot$s/g. In another embodiment of the present invention, the SFC of the SAPs is at least about $50 \times 10^{-7}$ cm$^3 \cdot$s/g. In yet another embodiment of the present invention, the SFC of the SAP is at least about $100 \times 10^{-7}$ cm$^3 \cdot$s/g. A method for determining the SFC of the SAP is provided hereafter in the Test Methods Section VIII.

Another important characteristic of the SAP of the present invention is its ability to swell against a load. This capacity versus a load is defined in terms of the SAP's Absorption Against Pressure (AAP) capacity. When an SAP is incorporated into an absorbent member at high concentrations, the polymer needs to be capable of absorbing large quantities of body fluids in a reasonable time period under usage pressures. Usage pressures exerted on the SAPs used within an AHP include both mechanical pressures (e.g., exerted by the weight and motions of a wearer, taping forces, etc.) and capillary pressures (e.g., resulting from the acquisition component(s) in the absorbent core that temporarily hold fluid before it is absorbed by the SAP).

In one embodiment of the present invention, the AAP of the SAP is at least about 15 g/g. In another embodiment of the present invention, the AAP of the SAP is at least about 20 g/g. In yet another embodiment of the present invention, the AAP of the SAP is from about 15 g/g to about 25 g/g. In even yet another embodiment of the present invention, the AAP of the SAP is from about 17 g/g to about 23 g/g. In one embodiment of the present invention, the AAP of the SAP is from about 20 g/g to about 23 g/g. A method for determining the AAP of the SAP is provided hereafter in the Test Methods Section VIII.

In one embodiment of the present invention, a method for providing an absorbent hygiene product (AHP) to a consumer comprises: a) providing a superabsorbent polymer (rSAP) made by the steps of: (i) separating a recycled SAP (rSAP) from a recycled AHP (rAHP); (ii) degrading said rSAP to a degraded material comprising poly(acrylic acid) (PAA); and (iii) polymerizing an acrylic acid in the presence of said PAA to form said SAP exhibiting an Absorption Against Pressure (AAP) of at least about 15 g/g. In another embodiment of the present invention, the AAP is at least about 20 g/g. In yet another embodiment of the present invention, the SAP exhibits a saline flow conductivity (SFC) of at least about $30 \times 10^{-7}$ cm$^3 \cdot$s/g. In even yet another embodiment of the present invention, the SFC is at least about $50 \times 10^{-7}$ cm$^3 \cdot$s/g. In one embodiment of the present invention, a method for providing an absorbent hygiene product (AHP) to a consumer comprises: a) providing a superabsorbent polymer (rSAP) made by the steps of: (i) separating a recycled SAP (rSAP) from a recycled AHP (rAHP); (ii) degrading said rSAP to a degraded material comprising poly(acrylic acid) (PAA); and (iii) polymerizing an acrylic acid in the presence of said PAA to form said SAP exhibiting an Absorption Against Pressure (AAP) of at least about 15 g/g and a saline flow conductivity (SFC) of at least about $30 \times 10^{-7}$ cm$^3 \cdot$s/g.

B. Polyolefins—Olefins derived from renewable or recycled resources may be polymerized to yield polyolefins. Ethylene derived from renewable resources may be polymerized under the appropriate conditions to prepare polyethylene having desired characteristics for use in a particular component of an AHP or in the packaging for said AHP. The polyethylene may be high density, medium density, low density, or linear-low density. Polyethylene and/or polypropylene may be produced via free-radical polymerization techniques, or by using Ziegler-Natta catalysis or metallocene catalysts. Polyolefins may be produced from solvent-based recycling (e.g. purification disclosed in U.S. Pat. Nos. 10,442,912; 10,450,436; and 10,465,058) or chemical recycling (i.e., pyrolysis and gasification) of waste polyolefins.

The polyolefin may be processed according to methods known in the art into a form suitable for the end use of the polymer. Suitable forms for polyolefins include a film, an apertured film, a microporous film, a fiber, a filament, a nonwoven, or a laminate. Suitable nonwoven forms include spunbond webs, meltblown webs, and combinations thereof (e.g., spunbond-meltblown webs (SM), spunbond-meltblown-spunbond webs (SMS), etc.). The polyolefin may comprise mixtures or blends with other polymers, such as polyolefins derived from petrochemicals. Depending on the end use and form, the polyolefin may comprise other compounds, such as inorganic compounds, fillers, pigments, dyes, antioxidants, UV stabilizers, binders, surfactants, wetting agents, and the like. For example, a polyolefin film may be impregnated with inorganic compound, such as calcium carbonate, titanium dioxide, clays, silicas, zeolites, kaolin, mica, carbon, and mixtures thereof. Such compounds may serve as pore forming agents which, upon straining the film, may improve the breathability of the film. This process is described further in U.S. Pat. No. 6,605,172. A binder may be used with polyolefin fibers, filaments, or nonwoven web. A suitable binder is a styrene-butadiene latex binder available under the trade name GENFLO™ 3160 (OMNOVA Solutions, Inc.; Akron, OH). The resulting binder/polyolefin web may be used as an acquisition layer, which may be associated with the absorbent core. The polyolefin materials and particularly polyolefin fibers, filaments, and nonwoven webs may treated with a surfactant or wetting agent, such as Irgasurf™ (Ciba Specialty Chemicals, Inc.; Tarrytown, NY).

Polyolefin nonwovens useful in an AHP may have a basis weight between about 1 g/m$^2$ and about 50 g/m$^2$ or between about 5 g/m$^2$ and about 30 g/m$^2$, as measured according to the Basis Weight Test provided below. Polyolefin nonwovens suitable for use as a topsheet may have an average liquid strike-through time of less than about 4 s, as measured according to the Liquid Strike-Through Test provided below. In other embodiments the polyolefin nonwoven may have an average strike-through time of less than about 3 s or less than about 2 s.

Polyolefin nonwoven useful as a barrier leg cuff may have a hydrohead of greater than about 5 mbar or about 6 mbar and less than about 10 mbar or about 8 mbar, as measured according to the Hydrohead test provided below.

Polyolefin films suitable for use as a backsheet may have an MD tensile strength of greater than about 0.5 N/cm or about 1 N/cm and less than about 6 N/cm or about 5 N/cm, as measured according to the Tensile Test as provided below. For breathable polyolefin films suitable for use as a backsheet, the film may have a Moisture Vapor Transmission Rate (MVTR) of at least about 2000 g/m$^2$/h, preferably greater than about 2,400 g/m$^2$/h, and even more preferably, greater than about 3,000 g/m$^2$/h, as measured by the Moisture Vapor Transmission Rate test provided below. It should be recognized that non-breathable backsheets, which are also useful in diapers, would exhibit an MVTR value of about 0 g/m$^2$/h.

In one embodiment of the present invention, a method for providing an absorbent hygiene product (AHP) to a consumer comprises combining a topsheet and a backsheet to define said AHP; wherein said topsheet and said backsheet are made from polyolefins; and wherein said polyolefins are made from waste polyolefins. In another embodiment of the present invention, said waste polyolefins are fed into a solvent-based purification process and produce virgin-like polyolefins.

C. Other Polymers—It should be recognized that any of the aforementioned polymers may be formed by using a combination of monomers derived from renewable resources and monomers derived from non-renewable (e.g., petroleum) resources. For example, the acrylic acid that will be polymerized and crosslinked into an SAP can be from a combination of acrylic acid derived from renewable resources and acrylic acid derived from non-renewable resources. The acrylic acid derived from a renewable resource may comprise at least about 5 wt % [weight of renewable resource monomer/weight of resulting polymer× 100], at least about 10 wt %, at least about 20 wt %, at least about 30 wt %, at least about 40 wt %, or at least about 50 wt % of the SAP.

IV. AHPs Comprising CycloSAP

The present invention relates to an AHP comprising a polymer derived from a recycled resource. The polymer has specific performance characteristics. The polymers derived from a recycled resource may be in any suitable form such as a film, nonwoven, SAP, and the like.

Figure 1B:
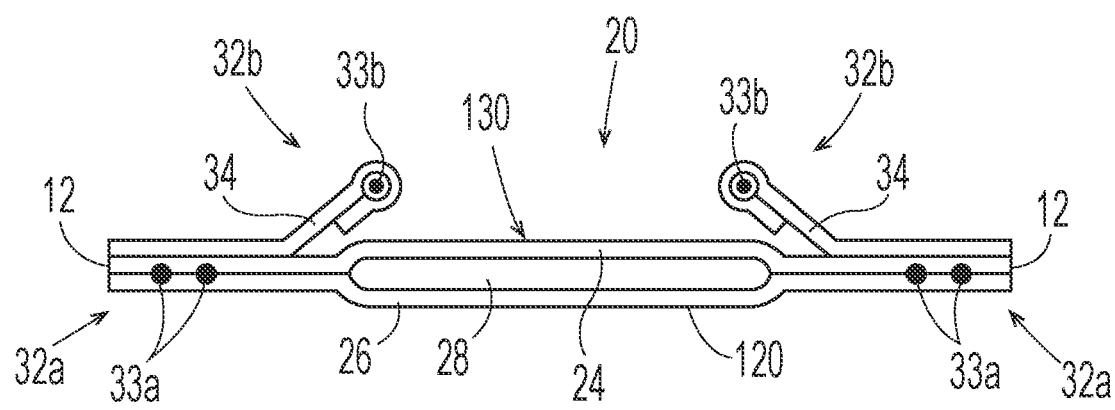
FIG. 1B is a cross-sectional view of the diaper of FIG. 1A taken along the lateral centerline.

FIG. 1A is a plan view of an exemplary, non-limiting embodiment of an AHP in the form of a diaper 20 in a flat, uncontracted state (i.e., without elastic induced contraction). The garment-facing surface 120 of the diaper 20 is facing the viewer and the body-facing surface 130 is opposite the viewer. The diaper 20 includes a longitudinal centerline 100 and a lateral centerline 110. FIG. 1B is a cross-sectional view of the diaper 20 of FIG. 1A taken along the lateral centerline 110. The diaper 20 may comprise a chassis 22. The diaper 20 and chassis 22 are shown to have a front waist region 36, a rear waist region 38 opposed to the front waist region 36, and a crotch region 37 located between the front waist region 36 and the rear waist region 38. The waist regions 36 and 38 generally comprise those portions of the diaper 20 which, when worn, encircle the waist of the wearer. The waist regions 36 and 38 may include elastic elements such that they gather about the waist of the wearer to provide improved fit and containment. The crotch region 37 is that portion of the diaper 20 which, when the diaper 20 is worn, is generally positioned between the legs of the wearer.

The outer periphery of diaper 20 and/or chassis 22 is defined by longitudinal edges 12 and lateral edges 14. The chassis 22 may have opposing longitudinal edges 12 that are oriented generally parallel to the longitudinal centerline 100. However, for better fit, longitudinal edges 12 may be curved or angled to produce, for example, an "hourglass" shape diaper when viewed in a plan view. The chassis 22 may have opposing lateral edges 14 that are oriented generally parallel to the lateral centerline 110.

The chassis 22 may comprises a liquid permeable topsheet 24, a backsheet 26, and an absorbent core 28 between the topsheet 24 and the backsheet 26. The absorbent core 28 may have a body-facing surface and a garment facing-surface. The topsheet 24 may be joined to the core 28 and/or the backsheet 26. The backsheet 26 may be joined to the core 28 and/or the topsheet 24. It should be recognized that other structures, elements, or substrates may be positioned between the core 28 and the topsheet 24 and/or backsheet 26. In certain embodiments, the chassis 22 comprises the main structure of the diaper 20 and other features may added to form the composite diaper structure. The topsheet 24, the backsheet 26, and the absorbent core 28 may be assembled in a variety of well-known configurations as described generally in U.S. Pat. Nos. 3,860,003; 5,151,092; 5,221,274; 5,554,145; 5,569,234; 5,580,411; and 6,004,306.

The absorbent core 28 may comprise the SAP derived from a recycled SAP of the present invention as well as a wide variety of other liquid-absorbent materials commonly used in diapers and other AHPs. Examples of suitable absorbent materials include comminuted wood pulp, which is generally referred to as air felt; chemically stiffened, modified or cross-linked cellulosic fibers; SAPs (also known as, absorbent gelling materials—AGMs); melt blown polymers, including co-form, bio soluble vitreous microfibers; tissue, including tissue wraps and tissue laminates; absorbent foams; absorbent sponges; and any other known absorbent material or combinations of materials. Exemplary absorbent structures for use as the absorbent core 28 are described in U.S. Pat. Nos. 4,610,678; 4,673,402; 4,834, 735; 4,888,231; 5,137,537; 5,147,345; 5,342,338; 5,260, 345; 5,387,207; 5,397,316; 5,625,222; and 6,932,800. Further exemplary absorbent structures may include non-removable absorbent core components and removable absorbent core components. Such structures are described in U.S. Patent Application Nos. 2004/0039361A1; 2004/ 0024379A1; 2004/0030314A1; 2003/0199844A1; and 2005/0228356A1. Ideally, the absorbent core 28 may be comprised entirely of materials derived from recycled SAP; however, the absorbent core 28 may comprise materials derived from recycled resources.

The absorbent core 28 may comprise a fluid acquisition component, a fluid distribution component, and a fluid storage component. A suitable absorbent core 28 comprising an acquisition layer, a distribution layer, and a storage layer is described in U.S. Pat. No. 6,590,136.

Another suitable absorbent core construction where the SAP of the present invention may be used is described in U.S. Patent Application No. 2004/0167486. The absorbent core of the aforementioned publication uses no or, in the alternative, minimal amounts of absorbent fibrous material within the core. Generally, the absorbent core may include no more than about 20 wt % of absorbent fibrous material (i.e., [weight of fibrous material/total weight of the absorbent core]×100). In one embodiment of the present invention, the AHP comprises an absorbent core, wherein said absorbent core comprises no more than about 20 wt % of an absorbent fibrous material.

The topsheet 24 is generally a portion of the diaper 20 that may be positioned at least in partial contact or close proximity to a wearer. Suitable topsheets 24 may be manufactured from a wide range of materials, such as woven or nonwoven webs of natural fibers (e.g., wood or cotton fibers), synthetic fibers (e.g., polyester or polypropylene fibers), or a combination of natural and synthetic fibers; apertured plastic films; porous foams or reticulated foams. The topsheet 24 is generally supple, soft feeling, and non-irritating to a wearer's skin. Generally, at least a portion of the topsheet 24 is liquid pervious, permitting liquid to readily penetrate through the thickness of the topsheet 24. Suitably, the topsheet 24 comprises a polymer (e.g. polyethylene) derived from a renewable resource or a recycled resource. Alternately, a suitable topsheet 24 is available from BBA Fiberweb (Brentwood, TN) as supplier code 055SLPV09U.

Any portion of the topsheet 24 may be coated with a lotion as is known in the art. Examples of suitable lotions include those described in U.S. Pat. Nos. 5,607,760; 5,609,587; 5,635,191; and 5,643,588. The topsheet 24 may be fully or partially elasticized or may be foreshortened so as to provide a void space between the topsheet 24 and the core 28. Exemplary structures including elasticized or foreshortened topsheets are described in more detail in U.S. Pat. Nos. 4,892,536; 4,990,147; 5,037,416; and 5,269,775.

The backsheet 26 is generally positioned such that it may be at least a portion of the garment-facing surface 120 of the diaper 20. Backsheet 26 may be designed to prevent the exudates absorbed by and contained within the diaper 20 from soiling articles that may contact the diaper 20, such as bed sheets and undergarments. In certain embodiments, the backsheet 26 is substantially water-impermeable; however, the backsheet 26 may be made breathable so as to permit vapors to escape while preventing liquid exudates from escaping. The polyethylene film may be made breathable by inclusion of inorganic particulate material and subsequent tensioning of the film. Breathable backsheets may include materials, such as woven webs, nonwoven webs, composite materials, such as film-coated nonwoven webs, and microporous films. Suitably, the backsheet 26 comprises a polymer such (e.g. polyethylene) derived from a recycled resource or a renewable resource as disclosed above. Alternative backsheets 26 derived from non-renewable resources include films manufactured by Tredegar Industries Inc. (Terre Haute, IN) and sold under the trade names X15306, X10962, and X10964; and microporous films such as manufactured by Mitsui Toatsu Co., of Japan under the designation ESPOIR NO and by EXXON Chemical Co., (Bay City, TX), under the designation EXXAIRE. Other alternative breathable backsheets 26 are described in U.S. Pat. Nos. 5,865,823; 5,571,096; and 6,107,537.

Backsheet 26 may also consist of more than one layer. For example, the backsheet 26 may comprise an outer cover and an inner layer or may comprise two outer layers with an inner layer disposed therebetween. The outer cover may have longitudinal edges and the inner layer may have longitudinal edges. The outer cover may be made of a soft, non-woven material. The inner layer may be made of a substantially water-impermeable film. The outer cover and an inner layer may be joined together by adhesive or any other suitable material or method. Suitably, the nonwoven outer cover and the water-impermeable film comprise polymers (e.g., polyethylene) may be derived from recycled or renewable resources. Alternatively, a suitable outer cover and inner layer derived from non-renewable resources are available, respectively, as supplier code A18AH0 from Corovin GmbH (Peine, Germany) and as supplier code PGBR4WPR from RKW Gronau GmbH (Gronau, Germany) While a variety of backsheet configurations are contemplated herein, it would be obvious to those skilled in the art that various other changes and modifications can be made without departing from the spirit and scope of the invention.

The diaper 20 may include a fastening system 50. When fastened, the fastening system 50 interconnects the front waist region 36 and the rear waist region 38. When fastened, the diaper 20 contains a circumscribing waist opening and two circumscribing leg openings. The fastening system 50 may comprise an engaging member 52 and a receiving member 54. The engaging member 52 may comprise hooks, loops, an adhesive, a cohesive, a tab, or other fastening mechanism. The receiving member 54 may comprise hooks, loops, a slot, an adhesive, a cohesive, or other fastening mechanism that can receive the engaging member 52. Suitable engaging member 52 and receiving member 54 combinations are well known in the art and include but are not limited to hooks/loop, hooks/hooks, adhesive/polymeric film, cohesive/cohesive, adhesive/adhesive, tab/slot, and button/buttonhole. Suitably, the fastening system 50 may comprise a polymer (e.g., polyethylene film or a polyethylene nonwoven) derived from recycled or renewable resources.

The diaper 20 may include front ears (not shown) and/or back ears 42. The front and/or back ears 42 may be unitary elements of the diaper 20 (i.e., they are not separately manipulative elements secured to the diaper 20, but rather are formed from and are extensions of one or more of the various layers of the diaper). In certain embodiments, the front and/or back ears 42 may be discrete elements that are joined to the chassis 22, as shown in FIG. 1A. Discrete front and/or back ears 42 may be joined to the chassis 22 by any bonding method known in the art such as adhesive bonding, pressure bonding, heat bonding, and the like. In other embodiments, the front and/or back ears 42 may comprise a discrete element joined to the chassis 22 with the chassis 22 having a layer, element, or substrate that extends over the front and/or back ear 42. The front ears and back ears 42 may be extensible, inextensible, elastic, or inelastic. The front ears and back ears 42 may be formed from nonwoven webs, woven webs, knitted fabrics, polymeric and elastomeric films, apertured films, sponges, foams, scrims, and combinations and laminates thereof. In certain embodiments the front ears and back ears 42 may be formed of a stretch laminate comprising a first nonwoven 42a, elastomeric material 42b, and, optionally, a second nonwoven 42c or other like laminates. The first and second nonwoven 42a, 42c may comprise a polymer (e.g., polyethylene) derived from a recycled or renewable resource. A suitable elastomeric material 42b may comprise a natural elastomer such as natural rubber or may comprise a synthetic elastomer such as the elastomeric film available from Tredegar Corp, Richmond, VA, as supplier code X25007. An alternate stretch laminate may be formed from the Tredegar X25007 elastomer disposed between two nonwoven layers (available from BBA Fiberweb, Brentwood, TN as supplier code FPN332).

The diaper 20 may further include leg cuffs 32a, 32b which provide improved containment of liquids and other body exudates. Leg cuffs 32a, 32b may also be referred to as gasketing cuffs, outer leg cuffs, leg bands, side flaps, elastic cuffs, barrier cuffs, second cuffs, inner leg cuffs, or "stand-up" elasticized flaps. U.S. Pat. No. 3,860,003 describes a disposable diaper which provides a contractible leg opening having a side flap and one or more elastic members to provide an elasticized leg cuff (i.e., a gasketing cuff). U.S. Pat. Nos. 4,808,178 and 4,909,803 describe disposable diapers having "stand-up" elasticized flaps (i.e., barrier cuffs) which improve the containment of the leg regions. U.S. Pat. Nos. 4,695,278 and 4,795,454 describe disposable diapers having dual cuffs, including gasketing cuffs and barrier cuffs.

FIGS. 1A-B shows the diaper 20 having dual cuffs: gasketing cuff 32a and barrier cuff 32b. The barrier cuff 32b may include one or more barrier elastic members 33b. The barrier elastic members 33b may be joined to a barrier cuff substrate 34. The barrier cuff substrate 34 may comprise a polymer derived from recycled or renewable resources. In certain embodiments, the barrier cuff substrate 34 may be a polymeric film or nonwoven. The barrier cuff 32b may be disposed on the body-facing surface of the chassis 22. The barrier cuff substrate 34 may extend laterally from the longitudinal edge 12 of the chassis 22 to a point inboard of the longitudinal edge 122. The barrier cuff 32b generally extends longitudinally at least through the crotch region 37. The barrier elastic members 33b allow a portion of the barrier cuff 32b to be spaced away from the body-facing surface of the diaper 20.

The gasketing cuff 32a may include one or more gasketing elastic members 33a. The gasketing elastic member 33a may be joined to one or more of the existing elements or substrates of the diaper 20 (e.g., topsheet 24, backsheet 26, barrier cuff substrate 34, etc.). In some embodiments, it may be desirable to treat all or a portion of the leg cuffs 32 with a hydrophilic surface coasting such as is described in U.S. Patent Application No. 2005/0177123A1. Suitable gasketing and barrier elastic members 33a, 33b include natural rubber, synthetic rubber, and other elastomers.

In other suitable embodiments, the diaper 20 may be pre-formed by the manufacturer to create a pant. A pant may be pre-formed by any suitable technique including, but not limited to, joining together portions of the product using re-fastenable and/or non-re-fastenable bonds (e.g., seam, weld, adhesive, cohesive bond, fastener, etc.). For example, the diaper 20 of FIG. 1A may be manufactured with the fastening system 50 engaged (i.e., the engaging member 52 is joined to the receiving member 54). As an additional example, the diaper 20 of FIG. 1A may be manufactured with the front ears 40 joined to the back ears 42 by way of a bond such as an adhesive bond, a mechanical bond, or some other bonding technique known in the art. Suitable pants are disclosed in U.S. Pat. Nos. 5,246,433; 5,569,234; 6,120,487; 6,120,489; 4,940,464; 5,092,861; 5,897,545; and 5,957,908.

In one embodiment of the present invention, a method for providing an absorbent hygiene product (AHP) to a consumer comprises: a) providing a superabsorbent polymer (SAP) made by the steps of: (i) separating a recycled SAP (rSAP) from a recycled AHP (rAHP); (ii) degrading said rSAP to a material comprising poly(acrylic acid) (PAA); and (iii) polymerizing an acrylic acid in the presence of said PAA to form said SAP exhibiting an Absorption Against Pressure (AAP) of at least about 15 g/g; and b) combining said SAP with AHP components comprising a topsheet and a backsheet to define said AHP. In another embodiment of the present invention, a method for providing an AHP to a consumer, said method comprises: a) providing a superabsorbent polymer (SAP) made by the steps of: (i) separating a recycled SAP (rSAP) from a recycled AHP (rAHP); (ii) degrading said rSAP to a material comprising poly(acrylic acid) (PAA) via processing in an extensional flow device; and (iii) polymerizing an acrylic acid in the presence of said PAA to form said SAP exhibiting an Absorption Against Pressure (AAP) of at least about 15 g/g and a saline flow conductivity (SFC) of at least about $30 \times 10^{-7}$ cm$^3$·s/g; and b) combining said SAP with AHP components comprising a topsheet and a backsheet to define said AHP.

V. Providing the AHP to a Consumer

Figure 2A:
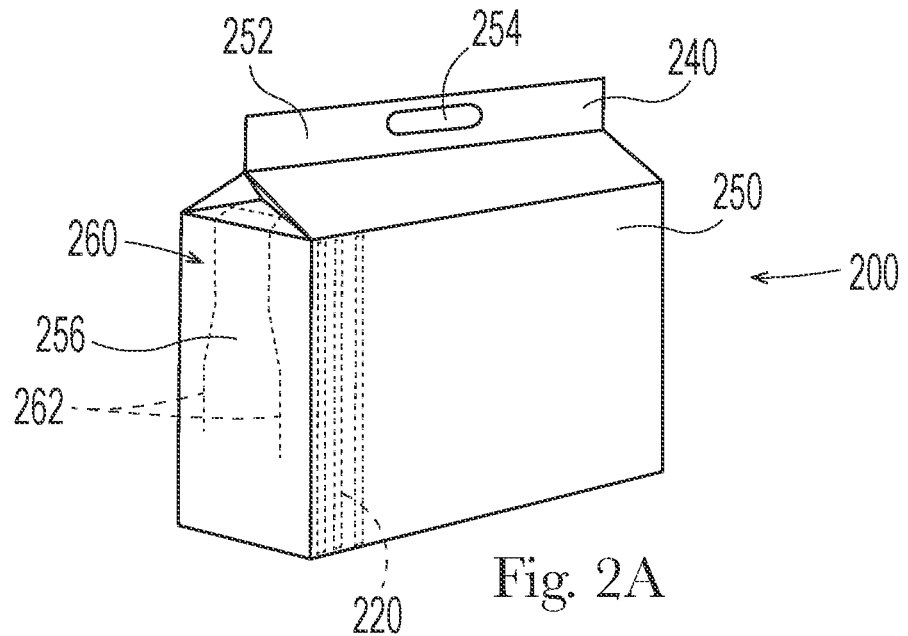
FIGS. 2A-B are perspective views of a package comprising an AHP.
Figure 2B:
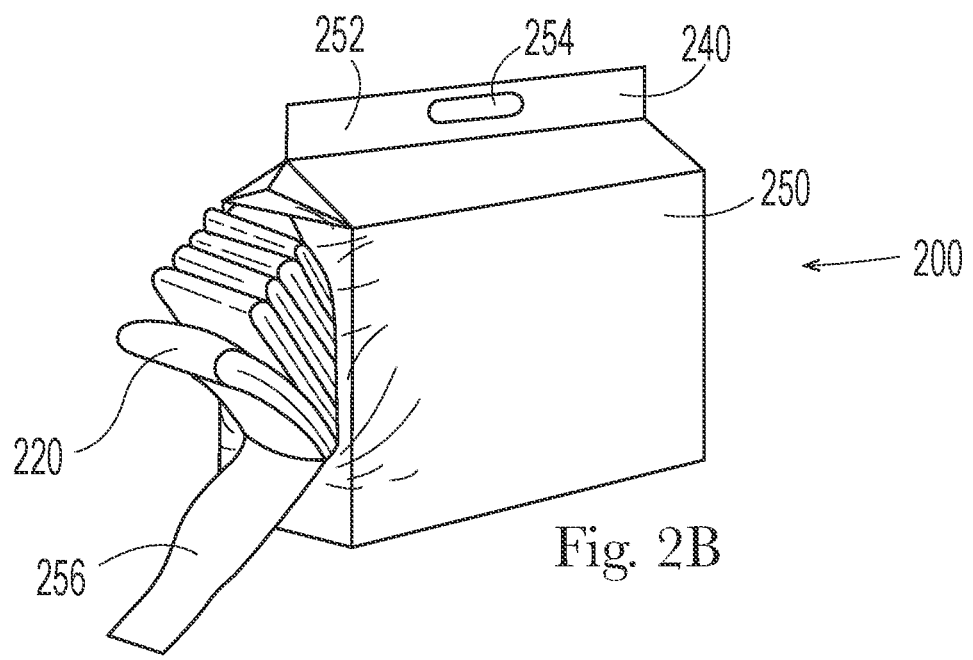

One or more AHPs (e.g., diapers) 220 may be provided as a package 200, as shown in FIGS. 2A-B. Generally, the package 200 allows for a quantity of AHPs 220 to be delivered to and purchased by a consumer while economizing space and simplifying transport and storage. The package 200 includes at least one AHP 220 secured by an overwrap 250. The overwrap 250 may partially or fully cover the AHPs, which may be compressed or uncompressed. FIG. 2A depicts an overwrap 250 that completely covers and encases a plurality of AHPs 220. The overwrap 250 may comprise a variety of materials including, but not limited to, thermoplastic films, nonwovens, wovens, foils, fabrics, papers, cardboard, elastics, cords, straps, and combinations thereof. Other suitable package structures and overwraps are described in U.S. Pat. Nos. 4,846,587; 4,934,535; 4,966,286; 5,036,978; 5,050,742; and 5,054,619. In certain embodiments, the overwrap 250 comprises a polymer (e.g., a polyolefin) derived from recycled or renewable resources. While the package 200 is not limited in shape, it may be desirable for the package 200 to have the shape of a parallelepiped or substantially similar to a parallelepiped (e.g., a solid at least a substantially planar base and four substantially planar sides). Such a shape is ideal for packaging, stacking, and transport. The package 200 is not limited in size; however, in certain embodiments, the size of the package 200 should be no greater than is required to contain the AHPs 220.

The package 200 may have a handle 240. In certain embodiments, the handle 240 may be a discrete element such as a strap that may be affixed to the overwrap 250. In the embodiment shown in FIGS. 2A-B, the handle 240 is integral to the overwrap 250. For this embodiment, the handle 240 may comprise an extension 252 from the overwrap 250. The extension 252 may have an aperture 254 there through. The aperture 254 ideally sized to permit entry by one or more digits of an adult hand.

An opening device 260 may be provided in the overwrap 250. For example, the opening device 260 may comprise a line of weakness 262 (e.g., perforations) in an overwrap 250 made from paper, cardboard, or film. The opening device 260 allows for partial or full removal of a flap 256 which is a portion of the overwrap 250. Partial of full removal of the flap 256 may allow for improved access to the AHPs 220. The opening device 260 and flap 256 are shown in a closed configuration in FIG. 2A and in an open configuration in FIG. 2B. An exemplary opening device 260 is presented in U.S. Pat. No. 5,036,978.

The package 200 may contain multiple overwraps 250. For example, a plurality of AHPs may be secured with a first overwrap such as a thermoplastic film and then a plurality of film wrapped AHPs may be secured in a second overwrap such as a cardboard box or another thermoplastic film.

In one embodiment of the present invention, a method for providing an absorbent hygiene product (AHP) to a consumer comprises: a) providing a superabsorbent polymer (SAP) made by the steps of: (i) separating a recycled SAP (rSAP) from a recycled AHP (rAHP); (ii) degrading said rSAP to a material comprising poly(acrylic acid) (PAA); and (iii) polymerizing an acrylic acid in the presence of said PAA to form said SAP exhibiting an Absorption Against Pressure (AAP) of at least about 15 g/g; b) combining said SAP with AHP components comprising a topsheet and a backsheet to define said AHP; and c) disposing said AHP into a package. In another embodiment of the present invention, a method for providing an AHP to a consumer, said method comprises: a) providing a superabsorbent polymer (SAP) made by the steps of: (i) separating a recycled SAP (rSAP) from a recycled AHP (rAHP); (ii) degrading said rSAP to a material comprising poly(acrylic acid) (PAA) via processing in an extensional flow device; and (iii) polymerizing an acrylic acid in the presence of said PAA to form said SAP exhibiting an Absorption Against Pressure (AAP) of at least about 15 g/g and a saline flow conductivity (SFC) of at least about $30 \times 10^{-7}$ cm$^3 \cdot$s/g; b) combining said SAP with AHP components comprising a topsheet and a backsheet to define said AHP; and c) disposing said AHP into a package.

VI. Communicating a Related Environmental Message to a Consumer

The present invention may further comprise a related environmental message or may further comprise a step of communicating a related environmental message to a consumer. The related environmental message may convey the benefits or advantages of the AHP comprising a polymer derived from recycled or renewable resources. The related environmental message may identify the AHPs as: being environmentally friendly or Earth friendly; having reduced petroleum (or oil) dependence or content; having reduced foreign petroleum (or oil) dependence or content; having reduced petrochemicals or having components that are petrochemical free; and/or being made from recycled or renewable resources or having components made from recycled or renewable resources. This communication is of importance to consumers that may have an aversion to petrochemical use (e.g., consumers concerned about depletion of natural resources or consumers who find petrochemical based products unnatural or not environmentally friendly) and to consumers that are environmentally conscious. Without such a communication, the benefit of the present invention may be lost on some consumers.

The communication may be affected in a variety of communication forms. Suitable communication forms include store displays, posters, billboard, computer programs, brochures, package literature, shelf information, videos, advertisements, internet web sites, pictograms, iconography, or any other suitable form of communication. The information could be available at stores, on television, in a computer-accessible form, in advertisements, or any other appropriate venue. Ideally, multiple communication forms may be employed to disseminate the related environmental message.

The communication may be written, spoken, or delivered by way of one or more pictures, graphics, or icons. For example, a television or internet based-advertisement may have narration, a voice-over, or other audible conveyance of the related environmental message. Likewise, the related environmental message may be conveyed in a written form using any of the suitable communication forms listed above. In certain embodiments, it may be desirable to quantify the reduction of petrochemical usage of the present AHP compared to AHPs that are presently commercially available.

Figure 3A:
FIGS. 3A-F are illustrations of several suitable embodiments of icons communicating reduced petrochemical dependence and/or environmental friendliness.
Figure 3B:
Figure 3C:
Figure 3D:
Figure 3E:
Figure 3F:
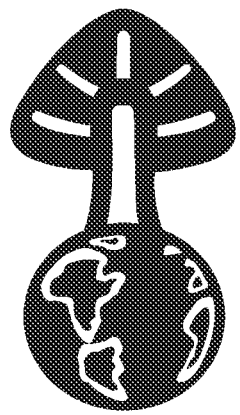

In other embodiments, the communication form may be one or more icons. FIGS. 3A-F depict several suitable embodiments of a communication in the form of icon 310. One or more icons 310 may be used to convey the related environmental message of reduced petrochemical usage. Suitable icons 310 communicating the related environmental message of reduced petroleum usage are shown in FIGS. 3A-B. Icons communicating the related environmental message of environmental friendliness, or recycled or renewable resource usage are shown in FIGS. 3C-F. In certain embodiments, the icons 310 may be located on the package 200 (as shown in FIGS. 2A-B) containing the AHPs, on the AHP, on an insert adjoining the package or the AHPs, or in combination with any of the other forms of the communication listed above.

The related environmental message may also include a message of petrochemical equivalence. As presented in the Background, many recycled or renewable, naturally occurring, or non-petroleum derived polymers have been disclosed. However, these polymers often lack the performance characteristics that consumers have come to expect when used in AHPs. Therefore, a message of petroleum equivalence may be necessary to educate consumers that the polymers derived from recycled or renewable resources, as described above, exhibit equivalent or better performance characteristics as compared to petroleum derived polymers. A suitable petrochemical equivalence message can include comparison to an AHP that does not have a polymer derived from recycled or renewable resources. For example, a suitable combined message may be, "Diaper Brand A with an environmentally friendly absorbent material is just as absorbent as Diaper Brand B." This message conveys both the related environmental message and the message of petrochemical equivalence.

In one embodiment of the present invention, a method for providing an absorbent hygiene product (AHP) to a consumer comprises: a) providing a superabsorbent polymer (SAP) made by the steps of: (i) separating a recycled SAP (rSAP) from a recycled AHP (rAHP); (ii) degrading said rSAP to a material comprising poly(acrylic acid) (PAA); and (iii) polymerizing an acrylic acid in the presence of said PAA to form said SAP exhibiting an Absorption Against Pressure (AAP) of at least about 15 g/g; b) combining said SAP with AHP components comprising a topsheet and a backsheet to define said AHP; c) disposing said AHP into a package; and d) communicating an environmental message to said consumer to convey that said AHP comprises material derived from a recycled resource. In another embodiment of the present invention, a method for providing an AHP to a consumer, said method comprises: a) providing a superabsorbent polymer (SAP) made by the steps of: (i) separating a recycled SAP (rSAP) from a recycled AHP (rAHP); (ii) degrading said rSAP to a material comprising poly(acrylic acid) (PAA) via processing in an extensional flow device; and (iii) polymerizing an acrylic acid in the presence of said PAA to form said SAP exhibiting an Absorption Against Pressure (AAP) of at least about 15 g/g and a saline flow conductivity (SFC) of at least about $30 \times 10^{-7}$ cm$^3 \cdot$s/g; b) combining said SAP with AHP components comprising a topsheet and a backsheet to define said AHP; c) disposing said AHP into a package; and d) communicating an environmental message to said consumer to convey that said AHP comprises material derived from a recycled resource. In yet another embodiment of the present invention, the environmental message is disposed on the package. In even yet another embodiment of the present invention, the environmental message is conveyed in an advertisement of said AHP.

VII. Method of Making an AHP Having CycloSAP

The present invention further relates to a method for making an AHP comprising an SAP derived from a recycled resource. The method comprises the steps of providing a recycled SAP (rSAP); degrading said rSAP to produce poly(acrylic acid) (PAA); polymerizing and crosslinking an acrylic acid in the presence of said PAA to form an SAP having a Saline Flow Conductivity of at least about $30 \times 10^{-7}$ cm$^3$·s/g and an Absorption Against Pressure of at least about 15 g/g; and incorporating said SAP into an AHP. The present invention further relates to providing one or more of the AHPs to a consumer and communicating reduced petrochemical usage to the consumer. The polymer derived from recycled resources may undergo additional process steps prior to incorporation into the AHP. Such process steps include drying, sieving, surface crosslinking, and the like.

VIII. Test Methods

Saline Flow Conductivity—The method to determine the permeability of a swollen hydrogel layer 718 is the "Saline Flow Conductivity" also known as "Gel Layer Permeability" and is described in several references, including, European Patent Application No. 640,330; U.S. patent application Ser. Nos. 11/349,696; 11/347,406; and Ser. No. 06/682,483; and U.S. Pat. No. 4,469,710. The equipment used for this method is described below.

Figure 4:
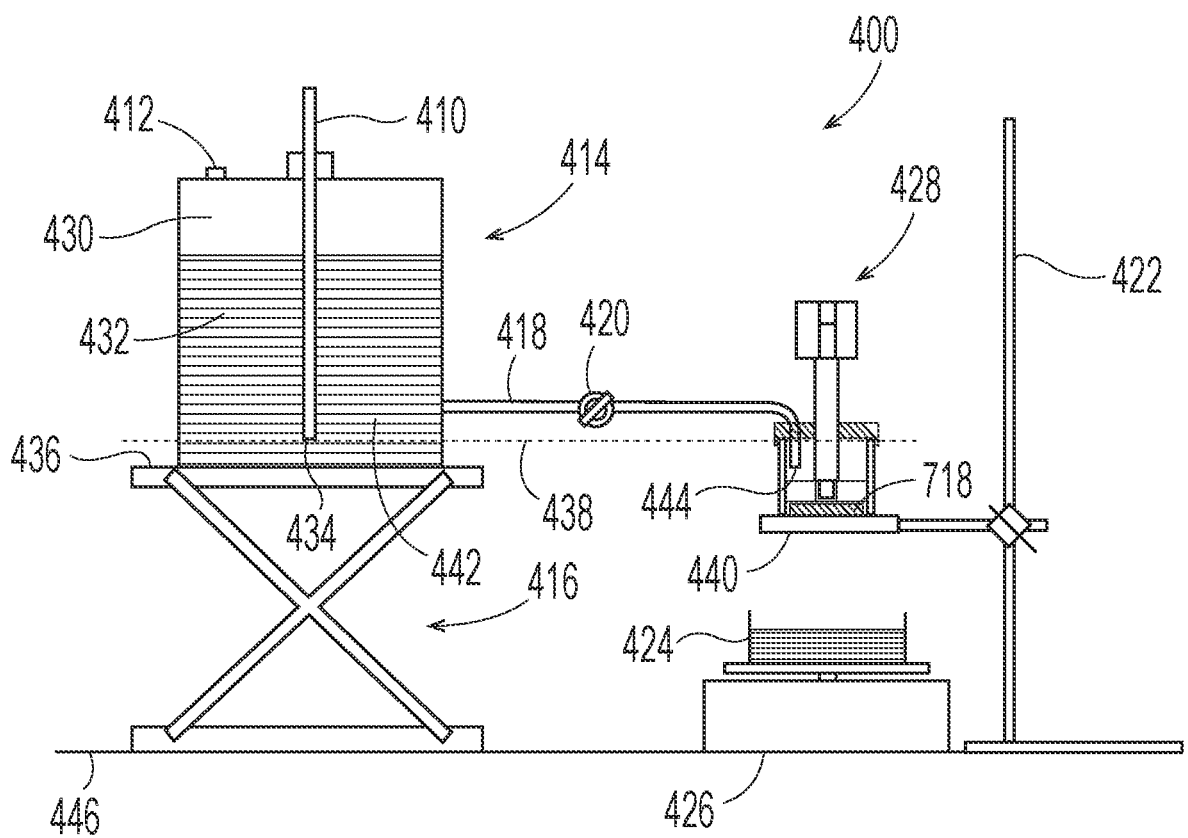
FIG. 4 is a partial cross-sectional side view of a suitable permeability measurement system for conducting the Saline Flow Conductivity Test.

Permeability Measurement System—FIG. 4 shows permeability measurement system 400 set-up with the constant hydrostatic head reservoir 414, open-ended tube for air admittance 410, stoppered vent for refilling 412, laboratory jack 416, delivery tube 418, stopcock 420, ring stand support 422, receiving vessel 424, balance 426 and piston/cylinder assembly 428.

Figure 5:
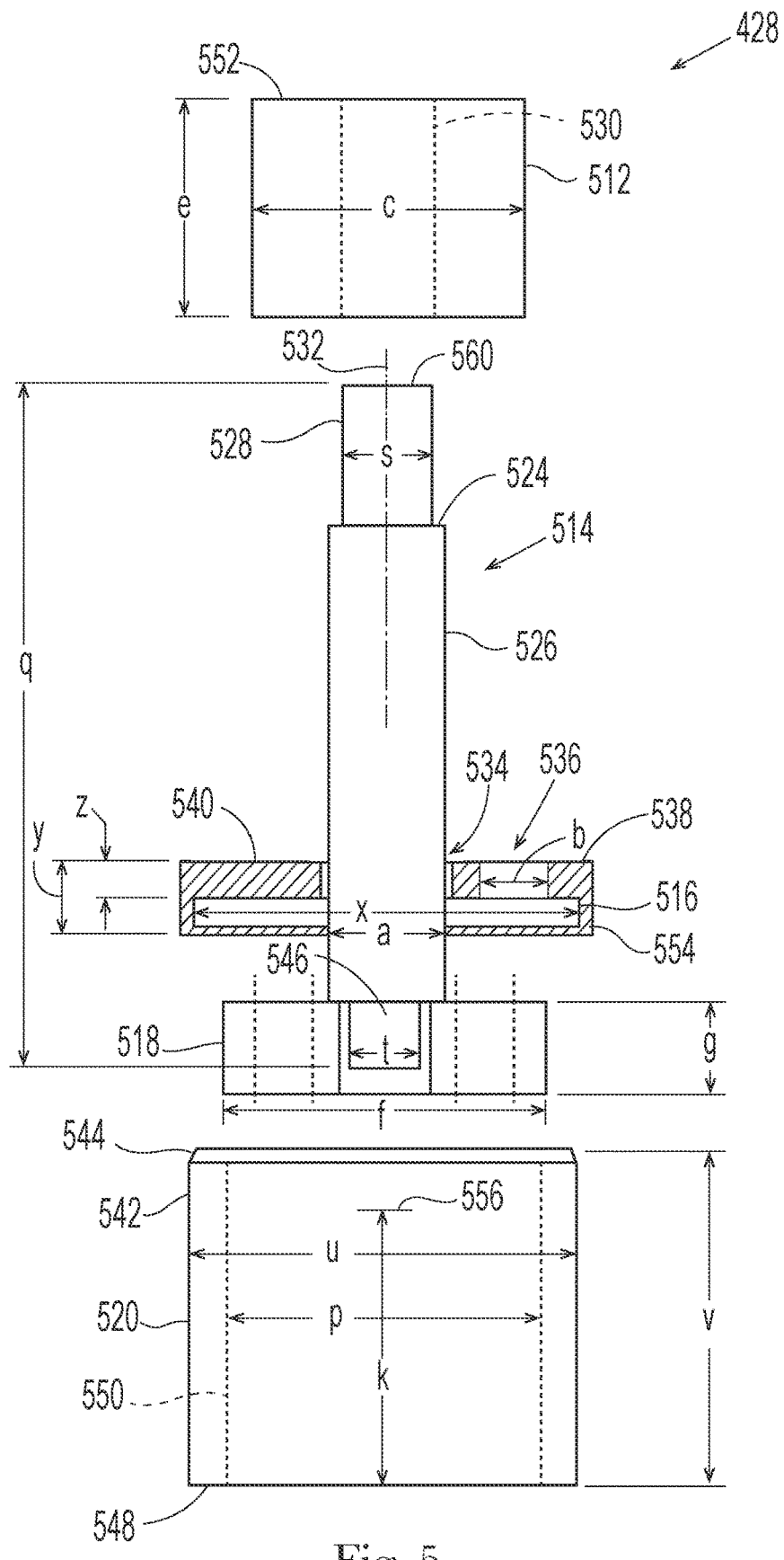
FIG. 5 is a cross-sectional side view of a piston/cylinder assembly for use in conducting the Saline Flow Conductivity Test.

FIG. 5 shows the piston/cylinder assembly 428 comprising a metal weight 512, piston shaft 514, piston head 518, lid 516, and cylinder 520. The cylinder 520 is made of transparent polycarbonate (e.g., Lexan®) and has an inner diameter (p) of 6.00 cm (area=28.27 cm$^2$) with inner cylinder walls 550 which are smooth. The bottom 548 of the cylinder 520 is faced with a U.S. Standard 400 mesh stainless-steel screen cloth (not shown) that is bi-axially stretched to tautness prior to attachment to the bottom 548 of the cylinder 520. The piston shaft 514 is made of transparent polycarbonate (e.g., Lexan®) and has an overall length q of approximately 127 mm A middle portion 526 of the piston shaft 514 has a diameter (r) of 21.15 mm. An upper portion 528 of the piston shaft 514 has a diameter (s) of 15.8 mm, forming a shoulder 524. A lower portion 546 of the piston shaft 514 has a diameter (t) of approximately ⅝ inch and is threaded to screw firmly into the center hole 618 (see FIG. 6) of the piston head 518. The piston head 518 is perforated, made of transparent polycarbonate (e.g., Lexan®), and is also screened with a stretched U.S. Standard 400 mesh stainless-steel screen cloth (not shown). The weight 512 is stainless steel, has a center bore 530, slides onto the upper portion 528 of piston shaft 514 and rests on the shoulder 524. The combined weight of the piston head 518, piston shaft 514 and weight 512 is 596 g (±6 g), which corresponds to 0.30 psi over the area of the cylinder 520. The combined weight may be adjusted by drilling a blind hole down a central axis 532 of the piston shaft 514 to remove material and/or provide a cavity to add weight. The cylinder lid 516 has a first lid opening 534 in its center for vertically aligning the piston shaft 514 and a second lid opening 536 near the edge 538 for introducing fluid from the constant hydrostatic head reservoir 414 into the cylinder 520.

A first linear index mark (not shown) is scribed radially along the upper surface 552 of the weight 512, the first linear index mark being transverse to the central axis 532 of the piston shaft 514. A corresponding second linear index mark (not shown) is scribed radially along the top surface 560 of the piston shaft 514, the second linear index mark being transverse to the central axis 532 of the piston shaft 514. A corresponding third linear index mark (not shown) is scribed along the middle portion 526 of the piston shaft 514, the third linear index mark being parallel with the central axis 532 of the piston shaft 514. A corresponding fourth linear index mark (not shown) is scribed radially along the upper surface 540 of the cylinder lid 516, the fourth linear index mark being transverse to the central axis 532 of the piston shaft 514. Further, a corresponding fifth linear index mark (not shown) is scribed along a lip 554 of the cylinder lid 516, the fifth linear index mark being parallel with the central axis 532 of the piston shaft 514. A corresponding sixth linear index mark (not shown) is scribed along the outer cylinder wall 542, the sixth linear index mark being parallel with the central axis 532 of the piston shaft 514. Alignment of the first, second, third, fourth, fifth, and sixth linear index marks allows for the weight 512, piston shaft 514, cylinder lid 516, and cylinder 520 to be re-positioned with the same orientation relative to one another for each measurement.

The cylinder 520 specification details are: Outer diameter (u) of the Cylinder 520: 70.35 mm; Inner diameter (p) of the Cylinder 520: 60.0 mm; and Height (v) of the Cylinder 520: 60.5 mm. The cylinder lid 516 specification details are: Outer diameter (w) of cylinder lid 516: 76.05 mm; Inner diameter (x) of cylinder lid 516: 70.5 mm; Thickness (y) of cylinder lid 516 including lip 554: 12.7 mm; Thickness (z) of cylinder lid 516 without lip: 6.35 mm; Diameter (a) of first lid opening 534: 22.25 mm; Diameter (b) of second lid opening 536: 12.7 mm; and Distance between centers of first and second lid openings 534 and 536: 23.5 mm. The weight 512 specification details are: Outer diameter (c): 50.0 mm; Diameter (d) of center bore 530: 16.0 mm; and Height (e): 39.0 mm. The piston head 518 specification details are: Diameter (f): 59.7 mm; Height (g): 16.5 mm; Outer holes 614 (14 total) with a 9.65 mm diameter (h), outer holes 614 equally spaced with centers being 47.8 mm from the center of center hole 618; Inner holes 616 (7 total) with a 9.65 mm diameter (i), inner holes 616 equally spaced with centers being 26.7 mm from the center of center hole 618; and Center hole 618 has a diameter (j) of ⅝ inches and is threaded to accept a lower portion 546 of piston shaft 514.

Prior to use, the stainless-steel screens (not shown) of the piston head 518 and cylinder 520 should be inspected for clogging, holes or over-stretching and replaced when necessary. An SFC apparatus with damaged screen can deliver erroneous SFC results and must not be used until the screen has been replaced.

A 5.00 cm mark 556 is scribed on the cylinder 520 at a height (k) of 5.00 cm (±0.05 cm) above the screen (not shown) attached to the bottom 548 of the cylinder 520. This marks the fluid level to be maintained during the analysis. Maintenance of correct and constant fluid level (hydrostatic pressure) is critical for measurement accuracy.

A constant hydrostatic head reservoir 414 is used to deliver salt solution 432 to the cylinder 520 and to maintain the level of salt solution 432 at a height (k) of 5.00 cm above the screen (not shown) attached to the bottom 548 of the cylinder 520. The bottom 434 of the air-intake tube 410 is positioned so as to maintain the salt solution 432 level in the cylinder 520 at the required 5.00 cm height (k) during the measurement, i.e., bottom 434 of the air tube 410 is in approximately same plane 438 as the 5.00 cm mark 556 on the cylinder 520 as it sits on the support screen (not shown) on the ring stand 440 above the receiving vessel 424. Proper height alignment of the air-intake tube 410 and the 5.00 cm mark 556 on the cylinder 520 is critical to the analysis. A suitable reservoir 414 consists of a jar 430 containing: a horizontally oriented L-shaped delivery tube 418 for fluid delivery, a vertically oriented open-ended tube 410 for admitting air at a fixed height within the constant hydrostatic head reservoir 414, and a stoppered vent 412 for re-filling the constant hydrostatic head reservoir 414. Tube 410 has an internal diameter of xx mm. The delivery tube 418, positioned near the bottom 442 of the constant hydrostatic head reservoir 414, contains a stopcock 420 for starting/stopping the delivery of salt solution 432. The outlet 444 of the delivery tube 418 is dimensioned to be inserted through the second lid opening 536 in the cylinder lid 516, with its end positioned below the surface of the salt solution 432 in the cylinder 520 (after the 5.00 cm height of the salt solution 432 is attained in the cylinder 520). The air-intake tube 410 is held in place with an O-ring collar (not shown). The constant hydrostatic head reservoir 414 can be positioned on a laboratory jack 416 in order to adjust its height relative to that of the cylinder 520. The components of the constant hydrostatic head reservoir 414 are sized so as to rapidly fill the cylinder 520 to the required height (i.e., hydrostatic head) and maintain this height for the duration of the measurement. The constant hydrostatic head reservoir 414 must be capable of delivering salt solution 432 at a flow rate of at least 3 g/s for at least 10 minutes.

The piston/cylinder assembly 428 is positioned on a 16-mesh rigid stainless-steel support screen (not shown) (or equivalent) which is supported on a ring stand 440 or suitable alternative rigid stand. This support screen (not shown) is sufficiently permeable so as to not impede salt solution 432 flow and rigid enough to support the stainless-steel mesh cloth (not shown) preventing stretching. The support screen (not shown) should be flat and level to avoid tilting the piston/cylinder assembly 428 during the test. The salt solution 432 passing through the support screen (not shown) is collected in a receiving vessel 424, positioned below (but not supporting) the support screen (not shown). The receiving vessel 424 is positioned on the balance 426 which is accurate to at least 0.01 g. The digital output of the balance 426 is connected to a computerized data acquisition system (not shown).

Preparation of Reagents (not illustrated)—Jayco Synthetic Urine (JSU) 712 (see FIG. 7) is used for a swelling phase (see SFC Procedure below) and 0.118 M Sodium Chloride (NaCl) Solution is used for a flow phase (see SFC Procedure below). The following preparations are referred to a standard 1-liter volume. For preparation of volumes other than 1 liter, all quantities are scaled accordingly.

JSU: A 1 L volumetric flask is filled with distilled water to 80% of its volume, and a magnetic stir bar is placed in the flask. Separately, using a weighing paper or beaker the following amounts of dry ingredients are weighed to within ±0.01 g using an analytical balance and are added quantitatively to the volumetric flask in the same order as listed below. The solution is stirred on a suitable stir plate until all the solids are dissolved, the stir bar is removed, and the solution diluted to 1 L volume with distilled water. A stir bar is again inserted, and the solution stirred on a stirring plate for a few minutes more.

Quantities of salts to make 1 liter of Jayco Synthetic Urine: Potassium Chloride (KCl) 2.00 g; Sodium Sulfate ($Na_2SO_4$) 2.00 g; Ammonium dihydrogen phosphate ($NH_4H_2PO_4$) 0.85 g; Ammonium phosphate, dibasic (($NH_4)_2$ $HPO_4$) 0.15 g; Calcium Chloride ($CaCl_2$) 0.19 g—[or hydrated calcium chloride ($CaCl_2.2H_2O$) 0.25 g]; and Magnesium chloride ($MgCl_2$) 0.23 g—[or hydrated magnesium chloride ($MgCl_2.6H_2O$) 0.50 g]

To make the preparation faster, each salt is completely dissolved before adding the next one. Jayco synthetic urine may be stored in a clean glass container for 2 weeks. The solution should not be used if it becomes cloudy. Shelf life in a clean plastic container is 10 days.

0.118 M Sodium Chloride (NaCl) Solution: 0.118 M NaCl is used as salt solution 432. Using a weighing paper or beaker 6.90 g (±0.01 g) of sodium chloride is weighed and quantitatively transferred into a 1 L volumetric flask; and the flask is filled to volume with distilled water. A stir bar is added, and the solution is mixed on a stirring plate until all the solids are dissolved.

Test Preparation—Using a solid reference cylinder weight (not shown) (40 mm diameter; 140 mm height), a caliper gauge (not shown) (e.g., Mitotoyo Digimatic Height Gage) is set to read zero. This operation is conveniently performed on a smooth and level bench top 446. The piston/cylinder assembly 428 without SAP is positioned under the caliper gauge (not shown) and a reading, $L_1$, is recorded to the nearest 0.01 mm.

The constant hydrostatic head reservoir 414 is filled with salt solution 432. The bottom 434 of the air-intake tube 410 is positioned so as to maintain the top part (not shown) of the liquid meniscus (not shown) in the cylinder 520 at the 5.00 cm mark 556 during the measurement. Proper height alignment of the air-intake tube 410 at the 5.00 cm mark 556 on the cylinder 520 is critical to the analysis.

The receiving vessel 424 is placed on the balance 426 and the digital output of the balance 426 is connected to a computerized data acquisition system (not shown). The ring stand 440 with a 16-mesh rigid stainless-steel support screen (not shown) is positioned above the receiving vessel 424. The 16-mesh screen (not shown) should be sufficiently rigid to support the piston/cylinder assembly 428 during the measurement. The support screen (not shown) must be flat and level.

SFC Procedure—0.9 g (±0.05 g) of an SAP is weighed onto a suitable weighing paper using an analytical balance. 0.9 g (±0.05 g) of SAP is weighed onto a suitable weighing paper using an analytical balance. The moisture content of the SAP is measured according to the EDANA Moisture Content Test Method 430.1-99 ("Superabsorbent materials-Polyacrylate superabsorbent powders-MOISTURE CONTENT–WEIGHT LOSS UPON HEATING" (February 99)). If the moisture content of the polymer is greater than 5%, then the polymer weight should be corrected for moisture (i.e., the added polymer should be 0.9 g on a dry-weight basis).

The empty cylinder 520 is placed on a level benchtop 446 and the SAP is quantitatively transferred into the cylinder 520. The SAP particles are evenly dispersed on the screen (not shown) attached to the bottom 548 of the cylinder 520 by gently shaking, rotating, and/or tapping the cylinder 520. It is important to have an even distribution of particles on the screen (not shown) attached to the bottom 548 of the cylinder 520 to obtain the highest precision result. After the SAP has been evenly distributed on the screen (not shown) attached to the bottom 548 of the cylinder 520 particles must not adhere to the inner cylinder walls 550. The piston shaft 514 is inserted through the first lid opening 534, with the lip 554 of the lid 516 facing towards the piston head 518. The piston head 518 is carefully inserted into the cylinder 520 to a depth of a few centimeters. The lid 516 is then placed onto the upper rim 544 of the cylinder 520 while taking care to keep the piston head 518 away from the SAP. The lid 516 and piston shaft 526 are then carefully rotated so as to align the third, fourth, fifth, and sixth linear index marks are then aligned. The piston head 518 (via the piston shaft 514) is then gently lowered to rest on the dry SAP. The weight 512 is positioned on the upper portion 528 of the piston shaft 514 so that it rests on the shoulder 524 such that the first and second linear index marks are aligned. Proper seating of the lid 516 prevents binding and assures an even distribution of the weight on the hydrogel layer 718.

Swelling Phase: An 8 cm diameter fritted disc (7 mm thick; e.g. Chemglass Inc. #CG 201-51, coarse porosity) 710 is saturated by adding excess JSU 712 to the fritted disc 710 until the fritted disc 710 is saturated. The saturated fritted disc 710 is placed in a wide flat-bottomed Petri dish 714 and JSU 712 is added until it reaches the top surface 716 of the fritted disc 710. The JSU height must not exceed the height of the fitted disc 710.

The screen (not shown) attached to the bottom 548 of the cylinder 520 is easily stretched. To prevent stretching, a sideways pressure is applied on the piston shaft 514, just above the lid 516, with the index finger while grasping the cylinder 520 of the piston/cylinder assembly 428. This "locks" the piston shaft 514 in place against the lid 516 so that the piston/cylinder assembly 428 can be lifted without undue force being exerted on the screen (not shown).

The entire piston/cylinder assembly 428 is lifted in this fashion and placed on the fritted disc 710 in the Petri dish 714. JSU 712 from the Petri dish 714 passes through the fritted disc 710 and is absorbed by the SAP (not shown) to form a hydrogel layer 718. The JSU 712 available in the Petri dish 714 should be enough for all the swelling phase. If needed, more JSU 712 may be added to the Petri dish 714 during the hydration period to keep the JSU 712 level at the top surface 716 of the fritted disc 710. After a period of 60 minutes, the piston/cylinder assembly 428 is removed from the fritted disc 710, taking care to lock the piston shaft 514 against the lid 516 as described above and ensure the hydrogel layer 718 does not lose JSU 712 or take in air during this procedure. The piston/cylinder assembly 428 is placed under the caliper gauge (not shown) and a reading, $L_2$, is recorded to the nearest 0.01 mm. If the reading changes with time, only the initial value is recorded. The thickness of the hydrogel layer 718, $L_0$ is determined from $L_2-L_1$ to the nearest 0.1 mm.

The entire piston/cylinder assembly 428 is lifted in this the fashion described above and placed on the support screen (not shown) attached to the ring stand 440. Care should be taken so that the hydrogel layer 718 does not lose JSU 712 or take in air during this procedure. The JSU 712 available in the Petri dish 714 should be enough for all the swelling phase. If needed, more JSU 712 may be added to the Petri dish 714 during the hydration period to keep the JSU 712 level at the 5.00 cm mark 556. After a period of 60 minutes, the piston/cylinder assembly 428 is removed, taking care to lock the piston shaft 514 against the lid 516 as described above. The piston/cylinder assembly 428 is placed under the caliper gauge (not shown) and the caliper (not shown) is measured as $L_2$ to the nearest 0.01 mm. The thickness of the hydrogel layer 718, $L_0$ is determined from $L_2-L_1$ to the nearest 0.1 mm. If the reading changes with time, only the initial value is recorded.

The piston/cylinder assembly 428 is transferred to the support screen (not shown) attached to the ring support stand 440 taking care to lock the piston shaft 514 in place against the lid 516. The constant hydrostatic head reservoir 414 is positioned such that the delivery tube 418 is placed through the second lid opening 536. The measurement is initiated in the following sequence:

a) The stopcock 420 of the constant hydrostatic head reservoir 410 is opened to permit the salt solution 432 to reach the 5.00 cm mark 556 on the cylinder 520. This salt solution 432 level should be obtained within 10 s of opening the stopcock 420.

b) Once 5.00 cm of salt solution 432 is attained, the data collection program is initiated.

With the aid of a computer (not shown) attached to the balance 426, the quantity of salt solution 432 passing through the hydrogel layer 718 is recorded at intervals of 20 s for a time period of 10 minutes. At the end of 10 minutes, the stopcock 420 on the constant hydrostatic head reservoir 410 is closed. The piston/cylinder assembly 428 is removed immediately, placed under the caliper gauge (not shown) and a reading, $L_3$, is recorded to the nearest 0.01 mm. The final thickness of the hydrogel layer 718, $L_f$ is determined from $L_3-L_1$ to the nearest 0.1 mm, as described above. The percent change in thickness of the hydrogel layer 718 is determined from $(L_f/L_0) \times 100$. Generally, the change in thickness of the hydrogel layer 718 is within about ±10%. The data from 60 s to the end of the experiment are used in the SFC calculation. The data collected prior to 60 s are not included in the calculation. The flow rate $F_s$ (in g/s) is the slope of a linear least-squares fit to a graph of the weight of salt solution 432 collected (in g) as a function of time (in seconds) from 60 s to 600 s.

In a separate measurement, the flow rate through the permeability measurement system 400 ($F_a$) is measured as described above, except that no hydrogel layer 718 is present. If $F_a$ is much greater than the flow rate through the permeability measurement system 400 when the hydrogel layer 718 is present, $F_s$, then no correction for the flow resistance of the permeability measurement system 400 (including the piston/cylinder assembly 428) is necessary. In this limit, $F_g = F_s$, where $F_g$ is the contribution of the hydrogel layer 718 to the flow rate of the permeability measurement system 400. However, if this requirement is not satisfied, then the following correction is used to calculate the value of $F_g$ from the values of $F_s$ and $F_a$:

$$F_g = (F_a \times F_s)/(F_a - F_s)$$

The Saline Flow Conductivity (K) of the hydrogel layer 718 is calculated using the following equation:

$$K = [F_g(t=0) \times L_0]/[\rho \times A \times \Delta P],$$

where $F_g$ is the flow rate in g/s determined from regression analysis of the flow rate results and any correction due to permeability measurement system 400 flow resistance, $L_0$ is the initial thickness of the hydrogel layer 718 in cm, $\rho$ is the density of the salt solution 432 in gm/cm³. A (from the equation above) is the area of the hydrogel layer 718 in cm², $\Delta P$ is the hydrostatic pressure in dyne/cm², and the saline flow conductivity, K, is in units of cm³·s/gm. The average of three determinations should be reported.

For hydrogel layers 718 where the flow rate is substantially constant, a permeability coefficient (K) can be calculated from the saline flow conductivity using the following equation:

$$\kappa = K\eta$$

where η is the viscosity of the salt solution 432 in poise and the permeability coefficient, κ, is in units of $cm^2$.

In general, flow rate need not be constant. The time-dependent flow rate through the system, $F_s(t)$ is determined, in units of g/s, by dividing the incremental weight of salt solution 432 passing through the permeability measurement system 400 (in g) by incremental time (in seconds). Only data collected for times between 60 s and 10 min is used for flow rate calculations. Flow rate results between 60 s and 10 min are used to calculate a value for $F_s$ (t=0), the initial flow rate through the hydrogel layer 718. $F_s$ (t=0) is calculated by extrapolating the results of a least-squares fit of $F_s(t)$ versus time to t=0.

Absorption Against Pressure—This test measures the amount of a 0.9% saline solution absorbed by SAPs that are laterally confined in a piston/cylinder assembly under a confining pressure for a period of one hour. European Disposables and Nonwovens Association (EDANA) test method 442.2-02 entitled "Absorption Under Pressure" is used.

Basis Weight—This test measures the mass per unit area for a substrate. European Disposables and Nonwovens Association (EDANA) test method 40.3-90 entitled "Mass Per Unit Area" is used.

Liquid Strike-Through—This test measures the time it takes for a known volume of liquid applied to the surface of a substrate to pass through the substrate to an underlying absorbent pad. European Disposables and Nonwovens Association (EDANA) test method 150.4-99 entitled "Liquid Strike-Through Time" is used.

Tensile Test—This test measures the peak load exhibited by a substrate. A preferred piece of equipment to do the test is a tensile tester such as an MTS Synergie100 or an MTS Alliance, fitted with a computer interface and Testworks 4 software, available from MTS Systems Corporation (14000 Technology Drive, Eden Prairie, MN, USA). This instrument measures the Constant Rate of Extension in which the pulling grip moves at a uniform rate and the force measuring mechanism moves a negligible distance (less than 0.13 mm) with increasing force. The load cell is selected such that the measured loads (e.g., force) of the tested samples will be between 10 and 90% of the capacity of the load cell (typically a 25 N or 50 N load cell).

A 1×1-inch (2.5×2.5 cm) sample is die-cut from the substrate using an anvil hydraulic press die to cut the film with the die into individual samples. A minimum of three samples are created which are substantially free of visible defects such as air bubbles, holes, inclusions, and cuts. Each sample must have smooth and substantially defect-free edges. Testing is performed in a conditioned room having a temperature of 23° C. (±1° C.) and a relative humidity of 50% (±2%) for at least 2 h. Samples are allowed to equilibrate in the conditioned room for at least 2 h prior to testing.

Pneumatic jaws of the tensile tester, fitted with flat 2.54 cm-square rubber-faced grips, are set to give a gauge length of 2.54 cm. The sample is loaded with sufficient tension to eliminate observable slack, but less than 0.05N. The sample is extended at a constant crosshead speed of 25.4 cm/min until the specimen completely breaks. If the sample breaks at the grip interface or slippage within the grips is detected, then the data is disregarded, and the test is repeated with a new sample and the grip pressure is appropriately adjusted. Samples are run at least in triplicate to account for film variability.

The resulting tensile force-displacement data are converted to stress-strain curves. Peak load is defined as the maximum stress measured as a specimen is taken to break and is reported in Newtons per centimeter width (as measured parallel to the grips) of the sample. The peak load for a given substrate is the average of the respective values of each sample from the substrate.

Moisture Vapor Transmission Rate (MVTR) Test—The MVTR test method measures the amount of water vapor that is transmitted through a film under specific temperature and humidity. The transmitted vapor is absorbed by $CaCl_2$ desiccant and determined gravimetrically. Samples are evaluated in triplicate, along with a reference film sample of established permeability (e.g., Exxon Exxaire microporous material #XBF-110W) that is used as a positive control.

This test uses a flanged cup machined from Delrin (Mc-Master-Carr Catalog #8572K34) and anhydrous $CaCl_2$ (Wako Pure Chemical Industries, Richmond, VA; Catalog 030-00525).

The height of the cup is 55 mm with an inner diameter of 30 mm and an outer diameter of 45 mm. The cup is fitted with a silicone gasket and lid containing 3 holes for thumb screws to completely seal the cup.

The cup is filled with $CaCl_2$ to within 1 cm of the top. The cup is tapped on the counter 10 times, and the $CaCl_2$ surface is leveled. The amount of $CaCl_2$ is adjusted until the headspace between the film surface and the top of the $CaCl_2$ is 1.0 cm. The film is placed on top of the cup across the opening (30 mm) and is secured using the silicone gasket, retaining ring, and thumb screws. Properly installed, the specimen should not be wrinkled or stretched.

The film must completely cover the cup opening, A, which is 0.0007065 $m^2$. The sample assembly is weighed with an analytical balance and recorded to ±0.001 g. The assembly is placed in a constant temperature (40±3° C.) and relative humidity (75±3%) chamber for 5.0 h±5 min. The sample assembly is removed, covered with Saran Wrap® and is secured with a rubber band. The sample is equilibrated to room temperature for 30 min, the plastic wrap removed, and the assembly is re-weighted, and the weight is recorded to ±0.001 g. The absorbed moisture $M_a$ is the difference in initial and final assembly weights. MVTR, in $g/m^2/24$ h, is calculated as:

$$MVTR = \frac{(M_a \times 24)}{(A \times 5 \text{ hours})}$$

Replicate results are averaged and rounded to the nearest 100 $g/m^2/24$ h, e.g., 2,865 $g/m^2/24$ h is herein given as 2,900 $g/m^2/24$ h and 275 $g/m^2/24$ h is given as 300 $g/m^2/24$ h.

IX. Examples

Example 1—Preparation of Cyclosap:
Polymerization and Crosslinking of Acrylic Acid in the Presence of PAA 10.54 g of distilled water and 105 g of 2.5 wt % PAA solution (produced from degrading a 2.5 wt % SAP gel) were charged to a 500 mL round bottom flange neck flask fitted with a 4-port flange lid and water-cooled condenser. The flask was cooled in an ice water bath. 43.18 g of Acrylic Acid (Cat #213040; 99.5%, low water, stabilized; Beantown Chemical) was added and stirred with a football shaped magnetic stirrer. 33.08 g of Sodium Hydroxide (Cat #415413; 50% in water; Sigma-Aldrich) mixed with 1.64 g of distilled water was added in small aliquots, keeping the temperature of the mixture between 17° C. and 30° C. After this addition the ice bath was removed. 0.335 g of polyethylene glycol diacrylate (Cat #455008; $M_n$ of 700 Da; Sigma-Aldrich) were dissolved in 3.16 g distilled water and added to the flask. The flask was purged with nitrogen for 1 h via a stainless-steel needle inserted via septum and bubbling into the stirred contents. 0.0113 g of L-Ascorbic Acid (Cat #A0278; Reagent Grade; Sigma-Aldrich) was dissolved in 0.5 mL distilled water and added to the flask. 0.0518 g of potassium persulfate (Cat #216224; ACS Reagent>99%; Sigma-Aldrich) and 0.0021 g of hydrogen peroxide (Stabilized, 1%, Kroger, Topical Solution USP) were dissolved in 2.5 mL distilled water and added to the flask within 1 min of the L-Ascorbic acid. The flask was observed and when the viscosity increased enough to stop the stirrer bar, the stirrer was switched off. Temperature was monitored and after the peak exotherm had been passed the condenser was removed, the flask was closed and placed in an oven at 60° C. for 18 h. The flask was removed, cooled and the gelled contents broken up by hand into pieces approximately 1 cm round and spread in an aluminum dish. The gel was dried in a fan oven at 120° C. for 6 h, removed, cooled and ground with an IKA All Basic S1 mill (IKA Works, Inc.). The ground powder was sieved and the fraction between 150 μm and 500 μm collected and placed in a controlled environment room at 73° F. and 50% relative humidity for 24 h.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any definition or meaning of a term in this written document conflicts with any definition or meaning of the term in a document incorporated by reference, the definition or meaning assigned to the term in this document shall govern.

What is claimed is:

1. A method for providing an absorbent hygiene product (AHP) to a consumer, said method comprising:
   a. providing a superabsorbent polymer (SAP) made by the steps of:
      i. separating a recycled SAP (rSAP) from a recycled AHP (rAHP);
      ii. degrading said rSAP to a material comprising poly(acrylic acid) (PAA); and
      iii. polymerizing an acrylic acid in the presence of said PAA to form said SAP exhibiting an Absorption Against Pressure (AAP) of at least about 15 g/g;
   b. combining said SAP with AHP components comprising a topsheet and a backsheet to define said AHP;
   c. disposing said AHP into a package; and
   d. communicating an environmental message to said consumer to convey that said AHP comprises material derived from a recycled resources;
   wherein the degrading comprises sonication.

2. The method of claim 1, wherein the degrading comprises UV irradiation in a flow system.

3. The method of claim 1, wherein the degrading comprises processing in an extensional flow device.

4. The method of claim 1, wherein the degrading comprises microwave-assisted hydrothermal processing.

5. The method of claim 1, wherein the degrading comprises oxidative degradation.

6. The method of claim 1, wherein said SAP exhibits a saline flow conductivity (SFC) of at least about $30 \times 10^{-7}$ cm$^3$·s/g.

7. The method of claim 6, wherein said SFC is at least about $50 \times 10^{-7}$ cm$^3$·s/g.

8. The method of claim 1, wherein said SAP exhibits an Absorption Against Pressure (AAP) of at least about 20 g/g.

9. The method of claim 1, wherein said acrylic acid is neutralized from about 50 mol % to about 95 mol %.

10. The method of claim 1, wherein said SAP is formed using a homogeneous solution polymerization process.

11. The method of claim 1, wherein said SAP is formed using a multi-phase polymerization process.

12. The method of claim 11, wherein said multi-phase polymerization process is selected from the group consisting of inverse emulsion processes and suspension polymerization processes.

13. The method of claim 1, wherein said SAP is formed by polymerization in the presence of a di- or poly-functional monomer.

14. The method of claim 1, further comprising surface crosslinking of said SAP.

15. The method of claim 1, wherein said AHP comprises an absorbent core; and wherein said absorbent core comprises no more than about 20 wt % of an absorbent fibrous material.

16. The method of claim 1, wherein the environmental message is disposed on the package.

17. The method of claim 1, wherein the environmental message is conveyed in an advertisement of said AHP.

18. A method for providing an AHP to a consumer, said method comprising:
   a. providing a superabsorbent polymer (SAP) made by the steps of:
      i. separating a recycled SAP (rSAP) from a recycled AHP (rAHP);
      ii. degrading said rSAP to a material comprising poly(acrylic acid) (PAA) via processing in an extensional flow device; and
      iii. polymerizing an acrylic acid in the presence of said PAA to form said SAP exhibiting an Absorption Against Pressure (AAP) of at least about 15 g/g and a saline flow conductivity (SFC) of at least about $30 \times 10^{-7}$ cm$^3$·s/g;
   b. combining said SAP with AHP components comprising a topsheet and a backsheet to define said AHP;
   c. disposing said AHP into a package; and
   d. communicating an environmental message to said consumer to convey that said AHP comprises material derived from a recycled resources;
      further comprising surface crosslinking of said SAP; wherein said acrylic acid is neutralized from about 50 mol % to about 95 mol %; and wherein said SAP is formed using a homogeneous solution polymerization in the presence of a di- or poly-functional monomer.

19. A method for providing an absorbent hygiene product (AHP) to a consumer, said method comprising:
   a. providing a superabsorbent polymer (SAP) made by the steps of:
      i. separating a recycled SAP (rSAP) from a recycled AHP (rAHP);
      ii. degrading said rSAP to a material comprising poly (acrylic acid) (PAA); and
      iii. polymerizing an acrylic acid in the presence of said PAA to form said SAP exhibiting an Absorption Against Pressure (AAP) of at least about 15 g/g;
   b. combining said SAP with AHP components comprising a topsheet and a backsheet to define said AHP;
   c. disposing said AHP into a package; and
   d. communicating an environmental message to said consumer to convey that said AHP comprises material derived from a recycled resource;
      wherein said SAP is formed using a multi-phase polymerization process.

20. The method of claim 19, wherein the degrading is selected from the group consisting of UV irradiation in a flow system, processing in an extensional flow device, microwave-assisted hydrothermal processing, sonication, oxidative degradation, and combinations thereof.

21. The method of claim 19, wherein said SAP exhibits a saline flow conductivity (SFC) of at least about $30 \times 10^{-7}$ $cm^3 \cdot s/g$.

22. The method of claim 19, wherein said SAP exhibits an Absorption Against Pressure (AAP) of at least about 20 g/g.

23. The method of claim 19, wherein said acrylic acid is neutralized from about 50 mol % to about 95 mol %.

24. The method of claim 19, wherein said multi-phase polymerization process is selected from the group consisting of inverse emulsion processes and suspension polymerization processes.

25. The method of claim 19, wherein said SAP is formed by polymerization in the presence of a di- or poly-functional monomer.

26. The method of claim 19, further comprising surface crosslinking of said SAP.

27. The method of claim 19, wherein said AHP comprises an absorbent core; and wherein said absorbent core comprises no more than about 20 wt % of an absorbent fibrous material.

* * * * *